US011505799B2

(12) United States Patent
Inapuri et al.

(10) Patent No.: US 11,505,799 B2
(45) Date of Patent: Nov. 22, 2022

(54) APTAMERS FOR MEASURING LIPOPROTEIN LEVELS

(71) Applicant: INNAMED, INC., Philadelphia, PA (US)

(72) Inventors: Eshwar Inapuri, Novi, MI (US); Anup Singh, Media, PA (US); Gregory Allen Penner, London (CA)

(73) Assignee: InnaMed, Inc., Philadelphia, PA (US)

( * ) Notice: Subject to any disclaimer, the term of this patent is extended or adjusted under 35 U.S.C. 154(b) by 243 days.

(21) Appl. No.: 16/629,223

(22) PCT Filed: Jul. 6, 2018

(86) PCT No.: PCT/US2018/040966
§ 371 (c)(1),
(2) Date: Jan. 7, 2020

(87) PCT Pub. No.: WO2019/010341
PCT Pub. Date: Jan. 10, 2019

(65) Prior Publication Data
US 2020/0131515 A1   Apr. 30, 2020

Related U.S. Application Data

(60) Provisional application No. 62/617,983, filed on Jan. 16, 2018, provisional application No. 62/529,600, filed on Jul. 7, 2017.

(51) Int. Cl.
*C12N 15/115* (2010.01)
*G01N 33/543* (2006.01)
*G01N 33/92* (2006.01)

(52) U.S. Cl.
CPC ..... *C12N 15/115* (2013.01); *G01N 33/54313* (2013.01); *G01N 33/92* (2013.01); *C12N 2310/16* (2013.01)

(58) Field of Classification Search
None
See application file for complete search history.

(56) References Cited

U.S. PATENT DOCUMENTS

| | | |
|---|---|---|
| 5,635,352 A | 6/1997 | Urdea et al. |
| 5,698,448 A | 12/1997 | Soldin |
| 6,264,825 B1 | 7/2001 | Blackburn et al. |
| 6,350,580 B1 | 2/2002 | Sorge |
| 6,361,944 B1 | 3/2002 | Mirkin et al. |
| 6,506,564 B1 | 1/2003 | Mirkin et al. |
| 6,750,016 B2 | 6/2004 | Mirkin et al. |
| 6,767,702 B2 | 7/2004 | Mirkin et al. |
| 6,773,884 B2 | 8/2004 | Mirkin et al. |
| 6,984,491 B2 | 1/2006 | Mirkin et al. |
| 7,005,265 B1 | 2/2006 | Fan et al. |
| 7,169,556 B2 | 1/2007 | Park et al. |
| 7,291,457 B2 | 11/2007 | Miller et al. |
| 7,803,542 B2 | 9/2010 | Xiao et al. |
| 7,807,352 B2 | 10/2010 | Rabbani et al. |
| 8,003,374 B2 | 8/2011 | Heeger et al. |
| 9,335,292 B2 | 5/2016 | Hu et al. |
| 2001/0024788 A1 | 9/2001 | Hashimoto |
| 2002/0006617 A1 | 1/2002 | Fan et al. |
| 2002/0012943 A1 | 1/2002 | Fowlkes et al. |
| 2002/0172953 A1 | 11/2002 | Mirkin et al. |
| 2003/0022150 A1 | 1/2003 | Sampson et al. |
| 2003/0077642 A1 | 4/2003 | Fritsch et al. |
| 2003/0108922 A1 | 6/2003 | Fritsch et al. |
| 2004/0106190 A1 | 6/2004 | Yang et al. |
| 2004/0191801 A1 | 9/2004 | Heeger et al. |
| 2005/0096288 A1 | 5/2005 | Guevara |
| 2005/0112605 A1 | 5/2005 | Heeger et al. |
| 2005/0164286 A1 | 7/2005 | Ouchi et al. |
| 2005/0202449 A1 | 9/2005 | Getts et al. |
| 2006/0228703 A1 | 10/2006 | Hartwich et al. |
| 2006/0234253 A1 | 10/2006 | Hasui et al. |
| 2007/0084721 A1 | 4/2007 | Hsung et al. |
| 2007/0236224 A1 | 10/2007 | Augustyniak et al. |
| 2008/0076139 A1 | 3/2008 | Singh |
| 2008/0302666 A1 | 12/2008 | Benner et al. |
| 2009/0042735 A1 | 2/2009 | Blair et al. |
| 2009/0305264 A1 | 12/2009 | West et al. |
| 2010/0035248 A1 | 2/2010 | Levicky et al. |
| 2010/0075319 A1 | 3/2010 | Lohse |
| 2010/0248231 A1 | 9/2010 | Wei et al. |
| 2010/0297654 A1 | 11/2010 | Heyduk |
| 2011/0053788 A1 | 3/2011 | Bamdad et al. |
| 2011/0143955 A1 | 6/2011 | Weiner |

(Continued)

FOREIGN PATENT DOCUMENTS

| | | |
|---|---|---|
| EP | 1198591 A1 | 4/2002 |
| EP | 1806414 A2 | 7/2007 |

(Continued)

OTHER PUBLICATIONS

De Crozals et al.; Methylene blue phosphoramidite for DNA labelling; ChemCommun; vol. 51(2); pp. 4458-4461; Mar. 14, 2014.

Garcia-Gonzalez et al.; Methylene blue covalently attached to single stranded DNA as electroactive label for potential bioassays; Sensors and Actuators B: Chemical; vol. 191; pp. 784-790; Feb. 1, 2014.

Arroyo-Curras et al.; Real-time measurement of small molecules directly in awake, ambulatory animals; Proceedings of the National Academy of Sciences; 114(4); pp. 645-650; Jan. 24, 2017.

Bonham et al.; Detection of IP-10 protein marker in undiluted blood serum via an electrochemical e-dna scaffold sensor; Analyst; 138(19); pp. 5580-5583; 9 pages (Author Manuscript); Oct. 7, 2013.

(Continued)

*Primary Examiner* — Sean McGarry
(74) *Attorney, Agent, or Firm* — Shay Glenn LLP

(57) ABSTRACT

Provided herein are aptamers for binding lipoproteins, systems for binding lipoproteins, and methods of detecting lipoproteins in a sample. The aptamers are useful for detecting the levels of lipoproteins in a biological sample and selectively detecting LDL particles in the presence of HDL particles. The aptamers can also be used as therapeutic agents against various diseases.

6 Claims, 11 Drawing Sheets

Specification includes a Sequence Listing.

(56) References Cited

U.S. PATENT DOCUMENTS

| | | |
|---|---|---|
| 2012/0021426 A1 | 1/2012 | Takoh et al. |
| 2012/0028242 A1 | 2/2012 | Heyduk et al. |
| 2015/0050645 A1 | 2/2015 | Takoh |
| 2018/0259483 A1 | 9/2018 | Easley et al. |
| 2019/0250120 A1 | 8/2019 | Korri-Youssoufi et al. |
| 2019/0382764 A1 | 12/2019 | Easley et al. |
| 2021/0055260 A1 | 2/2021 | Easley et al. |

FOREIGN PATENT DOCUMENTS

| | | |
|---|---|---|
| WO | WO01/040511 A2 | 6/2001 |
| WO | WO01/051665 A2 | 7/2001 |
| WO | WO01/073123 A2 | 10/2001 |
| WO | WO02/018643 A2 | 3/2002 |
| WO | WO02/046472 A2 | 6/2002 |
| WO | WO03/035829 A2 | 5/2003 |
| WO | WO2004/023128 A1 | 3/2004 |
| WO | WO2006/096185 A2 | 9/2006 |
| WO | WO2008/001376 A2 | 1/2008 |
| WO | WO2008/054517 A2 | 5/2008 |
| WO | WO2018/111745 A1 | 6/2008 |
| WO | WO2011/017382 A2 | 2/2011 |
| WO | WO2011/050069 A1 | 4/2011 |
| WO | WO2011/161420 A2 | 12/2011 |
| WO | WO2015/150482 A1 | 10/2015 |
| WO | WO2017/192737 A1 | 11/2017 |
| WO | WO2018/011412 A1 | 1/2018 |

OTHER PUBLICATIONS

Campos et al.; Amperometric detection of lactose using ?-galactosidase immobilized in layer films; ACS Applied Materials and Interfaces; 6(14); pp. 11657-11664; 8 pages (Author Manuscript); Jul. 11, 2014.

Carrillo et al.; The multiple sequence aligment problem in biology; SIAM Journal on Applied Mathematics; 48(5); pp. 1073-1082; Oct. 1988.

Cash et al.; An electrochemical sensor for the detection of protein-small molecule interactions directly in serum and other complex matrices; Journal of the American Chemical Society; 131(20); pp. 6955-6957; May 4, 2009.

Dirks et al.; A partition function algorithm for nucleic secondary structure including pseudoknots; Journal of Computational Chemisrty; 24(10); pp. 1664-1677; Oct. 2003.

Dirks et al.; An algorithm for computing nucleic acid base-pairing proabilities including pseudoknots; Journal of Computational Chemisrty; 25(10); pp. 1295-1304; Jul. 30, 2004.

Dirks et al.; Paradigms for computational nucleic acid design; Nucleic Acid Research; 32(4); pp. 1392-1403; Feb. 27, 2004.

Dryden et al.; Dstat: A versatile, open-source potentiostat for electroanalysis and integration; PLOS One; DOI: 10.1371/journal. pone.0140349; 17 pages; Oct. 28, 2015.

Fan et al.; Electrochemical interrogation of conformational changes as a reagentless method for the sequence-specific detection of dna; Proceedings of the National Academy of Sciecnes; 100(16); pp. 9134-9137; Aug. 5, 2003.

Ferapontova et al.; An rna aptamer-based electrochemical biosensor for detection of theophylline in serum; Journal of the American Chemical Society; 130(13); pp. 4256-4258; Apr. 2, 2008.

Ferguson et al.; Real-time, aptamer-based tracking of circulating therapeutic agents in living animals; Science Translational Medicine; 5(213); pp. 213ra165, 11 pages; Nov. 27, 2013.

Hu et al.; A reusable electruchemical proximity assay for highly selective, real-time protein quantitation in biological matrices; Journal of the American Chemical Society; 136(23); pp. 8467-8474; May 30, 2014.

Idili et al.; Folding-upon-binding and signal-on electrochemical dna sensor with high affinity and specificity; Analytical Chemistry; 86(18); pp. 9013-9019; Jul. 3, 2014.

Jeyarajah et al.; Lipoprotein particle analysis by nuclaer magnetic resoance spectroscopy; Clinics in Laboratory Medicine; 26(4); pp. 847-870; Dec. 2006.

Kaess et al.; The lipoprotein sub-fraction profile hertability and indentification of quantitative trait loci; Journal of Lipid Research; 49(4); pp. 715-723; Apr. 2008.

Kang et al.; Comparing the properties of electrochemical-based dna sensors employing different redox tags, Analytical Chemistry; 81(21); pp. 9109-9113; 12 pages (Author Manuscript); Oct. 7, 2009.

Kang et al.; Expanding the scope of protein-detecting electrchemical dna "scaffold" sensors; ACS Sensors; 3(7); pp. 1271-1275; 12 pages (Author Manuscript); Jun. 2018.

Kick et al.; EGNAS: an exhaustive dna sequence design aigoritlim; BMC Bioinformatics; 13(1); pp. 138; 17 pages; http://www.biomedcentral.com/1471-2105/13/138; Dec. 2012.

Labib et al.; Electrochemical methods for the analysis of clinically relevant biomolecules; Chemical Reviews; 116(16); pp. 9001-9090; Jul. 18, 2016.

Li et al.; Target-responsive structural switching for nucleic acid-based sensors, Accounts of Chemical Research; 43(5); pp. 631-641; Mar. 11, 2010.

Liu et al.; Aptamer-based electrochemical biosensors for interferon gamma detection; Analytical Chemistry; 82(19); pp. 8131-8136; Sep. 3, 2010.

MAGE; Closed-loop control of circulating drug levels in live animals; Nature Biomedical Engineering; 1(5); DOI:10.1038/s415551-017-0070, 10 pages; May 2017.

Mahshid el al.; A highly selective electrochemical dan-based sensor that employs steric hindrance effects to detect proteins directly in whole blood; Journal of the American Chemical Society; 137(50); pp. 15596-15599; Sep. 24, 2015.

Mahshid et al.; Biomolecular steric hindrance effects are enhanced on nanostructured microelectrodes; Analytical Chemistry; 89(18); pp. 9751-9757; Sep. 5, 2017.

Mahshid et al.; Electrochemical dna-based immunoassay that employs steric hindrance to detect small molecules directly in whole blood; AACS Sensors; 2(6); pp. 718-723; May 25, 2017.

Needleman et al.; A general method applicable to the search for similarities in the amino scid sequence of two proteins; Journal of Molecular Biology; 48(3); pp. 443-453; Mar. 1970.

Sacks et al.; Clinical review 163: cardiovascular endocrinology: low-density lipoprotein size and cardovascular disease: a reappraisal; The Journal of Clinical Endocrinology and Metabolism; 88(10); pp. 4525-4532; Oct. 2003.

Schoukroun-Barnes et al.; Reagentless, structure-switching, electrochemical aptamer-based sensors; Annual Review of Analtyical Chemistry; 9(1); pp. 163-181; 23 pages (Author Manuscript) Jun. 2016.

Sigma-Aldrich; Self-assembled monolayers: advantages of pure alkanethiols; 4 pages retrieved from the internet (https://www.sigmaaldrich.com/technical-documents/articles/material-matters/self-assembled-monolayers.html) on Dec. 10, 2019.

Silva et al.; Gold electrode modified by self-assembled monolayers of thiolis to determine dna sequences hybridization; Journal of Chemical Sciences; 122(6); pp. 911917; Nov. 2010.

Somasundaram et al.; Understanding signal and background in a thermally resolved, single-branched dna assay using sqaure wave voltammetry; Analytical Chemistry; 90(50); pp. 3584-3591; 18 pages (Author Manuscript); Jan. 31, 2018.

Turner; Biosensors: sense and sensibility; Chemical Society Reviews; 42(8); pp. 3184-3196; (year of pub. sufficiently earlier than effective US filing date and any foreign priority date) 2013.

White et al.; Exploiting binding changes in probe flexibility for the optimization of electrochemical biosensors; Analytical Chemistry; 82(1); pp. 73-76; 10 pages (Author Manuscript); Dec. 10, 2009.

Wolfe et al.; Constrained multistate sequence design for nucleic acid reaction pathway engineering; Journal of American Chemical Society; 139(8); pp. 3134-3144: Feb. 13, 2017.

Wolfe et al.; Sequence design for a test tube of interacting nucleic acid strands; ACS Synthetic Biology; 4(10); pp. 1086-1100; Oct. 20, 2014.

Xiao et al.; A reagentless signal-on architecture for electronic, aptamer-based sensors via target-induced strand displacement; Jour-

(56) References Cited

OTHER PUBLICATIONS nal of the American Chemical Society; 127(51); pp. 17990-17931; (Author Manuscript); Dec. 28, 2005.
Zadeh et al.; Nucleic acid sequence design via efficient ensemble defect optimization; Journal of Computational Chemistry; 32(3); pp. 439-452; Feb. 2011.
Zadeh et al.; NUPACK: analysis and design of nucleic acid systems; Journal of computattional Chemistry; 32(1); pp. 170-173; Jan. 15, 2011.
Zhou et al.; Steric hindrance assay for secreted factors in stem cell culture; ACS Sensors; 2(4); pp. 495-500; Apr. 17, 2017.
Zymek et al.; The role of platelet-derived growth factor signal in healing myocardial infarcts; Journal of the American college of Cardiology; 48(11); pp. 2315-2323; Dec. 5, 2006.
Baker et al.; An electronic aptamer-based small-molecule sensor for the rapid, label-free detection in adulterated samples and biological fluids; Journal of the American Chenical Society; 128(10); pp. 3138-3139; Mar. 2006.
Sheth et al.; Decapping and decay of messenger RNA occur in cytoplasmic processing bodies; Science; 300; pp. 805-808; May 2003.
Somasundaram et al.; U.S. Appl. No. 17/616,338 entitled "Assay method for point of care quantification of an immunophilin-binding immunosuppressant drug," filed Dec. 3, 2021.
Denman et al.; Continuous differential monitoring of the spend dialysate glucose level: clinical evaluation; Sensors and Actuators B: Chemical; 44 (1-3); pp. 304-308; Oct. 1, 1997.
Deng et al.; Sensitive bifunctional aptamer-based electrochemical biosensor for small molecules and protein; Analytical Chemistry; 81(24); pp. 9972-9978; Nov. 19, 2009.
Du et al.; Multifunctional label-free electrochemical biosensor based on an integrated aptamer; Analytical Chemistry; 80(13); pp. 5110-5117; Jun. 4, 2008.
Fan et al.; A Competitor-switched eleotrochemical sensor for detection of dna; Chin. J. Chem.; 28; pp. 1978-1982; (year of pub. sufficiently earlier than effective US filing date end any foreign priority date) 2010.
Huang et al.; Random wlak on a leash: a simple single-molecule diffusion model for surface-tethered redox molecules with flexible linkers; Journal of the American Chemical Society; 135(34); pp. 12808-12817; Aug. 20, 2013.
Li et al.; A simple assay to amplify the electrochemical signal by the aptamer based biosensor modified with CdS hollow nanospheres; Biosensors and Bioelectronics; 26(8); pp. 3531-3535; Apr. 15, 2011.

Lin et al.; Label-free aptamer-based electrochemical impedance biosensor for 17? estradiol; Analyst; 137(4); pp. 819-822; Feb. 2012.
Lu et al.; Aptamer-based electrochemical sensors that are not based on the target binding-induced conformational change of aptamers; Analyst; 133(9); pp. 1256-1260; Sep. 2008.
Lubin et al.; Effects of probe length, probe geometry, and redox-tag placement on the performance of the electtrochemical e-dna sensor; Analytical Chemistry; 81(6); pp. 2150-2158; Feb. 12, 2009.
Suna et al.; 1H NMR metabolomics of plasma lipoprotein subclasses: elucidation of metabolic clustering by self-organizing maps; NMR in Biomedicine; 20(7); pp. 658-672; Nov. 2007.
Tong et al.; Simply amplified electrochemical aptasensor of ochratoxin a based on exonuclease-catalyzed target; Biosensors and Bioelectronics; 29(1); pp. 97-101; Nov. 15, 2011.
Wang et al.; A sensitive ligase-based atp electrochemical assay using molecular beacon-like dna; Biosensor and Bioelectronics; 25(9); pp. 2101-2106; May 2010.
Wu et al.; Reusable electrochemical sensing platform for highly sensitive detection of small molecules based on structure-switching signal aptamers; Analytical Chemistry; 79(7); pp. 2933-2939; Apr. 2007.
Xiao et al.; Preparation of electrode-immobilized, redox-modified oligonucleotides for electrochemical dna and aptamer-based sensing; Nature Protocols; 2(11); pp. 2875-2880; Nov. 2007.
Yeung et al.; Electrochemical real-time polymerase chain reaction; Journal of the American Chemical Society; 128(41); pp. 13374-13375; Oct. 18, 2006.
Zhang et al.; Electrochemical aptasensor based on proximity-dependent surface hybridization assay for protein detection; Electroanalysis: An International Journal Devoted to Fundamental and Practical Aspects of Electroanalysis; 21(11); pp. 1327-1333; Jun. 2009.
Zhang et al., Electrochemical aptasensor based on proximity-dependent surface hybridization assay for single-step, reusable, sensitive protein detection; Journal of the American Chemical Society; 129(50); pp. 15448-15449; Published on line Nov. 22, 2007.
Zhao et al.; A label-free electrochemilumescent sensor for atp detection based on atp-dependent ligation; Talanta; 154; pp. 492-497; Jul. 2016.
Dirks et al.; Thermodynamic analysis of interacting nucleic acid strands; SIAM Rev.; 49(1); pp. 65-88; (year of pub. sufficiently earlier than effective US filing date and any foreign priority date) 2007.
Jakubowska; Signal processing in electrochemistry; Electroanalysis; 23(3); pp. 553-572; Mar. 2011.

Binding coefficient values for aptamers for large and fluffy LDL

Comparison of LDL-A1 and LDL-A274 with different types of LDL

APTAMERS FOR MEASURING LIPOPROTEIN LEVELS

CROSS-REFERENCE TO RELATED APPLICATIONS

This application claims the benefit of priority to U.S. Provisional Patent Application No. 62/617,983, filed on Jan. 16, 2018, and U.S. Provisional Patent Application No. 62/529,600 filed on Jul. 7, 2017.

REFERENCE TO SEQUENCE LISTING

The present application is being filed along with a Sequence Listing in electronic format. The Sequence Listing is provided as a file entitled InnaMed Sequences final.txt, created Jul. 6, 2018, which is approximately 4 KB in size. The information in the electronic format of the Sequence Listing is hereby incorporated by reference in its entirety.

BACKGROUND

Heart disease is a leading cause of death worldwide today. To tackle this important issue, medical personnel frequently measure blood analytes to help with the monitoring and prediction of heart disease. In many scenarios, a blood sample is taken at a date much earlier than the meeting with medical personnel so that laboratory testing may occur in time to facilitate a discussion of results at the meeting between the patient and medical personnel. However, because of this workflow, patient adherence often suffers because of the multiple necessary visits. In numerous cases, however, this overhead time and the associated costs can be eliminated by using point of care testing thus helping with adherence and increasing the number of conducted tests.

Furthermore, recent developments in research related to heart disease have determined that certain blood analytes may be more relevant to the prediction and monitoring of heart disease than the traditional biomarker panels. Typically, low-density lipoprotein (LDL) is thought to cause cardiovascular disease (CVD) by transporting cholesterol to the artery wall. Numerous studies exist showing the cholesterol carrying capacity of such molecules. However, it has been recently determined that LDL cholesterol (LDL-C) is only one property of LDL related particles and that LDL particle count (LDL-P) also affects the progression of CVD due to the differential diffusion properties of particles based on size, density and concentration.

In fact, in some scenarios, it has been determined that the measurement of LDL-P is more instructive in determining heart disease risk than measuring LDL-C. Therefore, it would be desirable to provide a point-of-care (POC) test that would test for LDL-P in conjunction with the traditional lipid panel (i.e. total cholesterol, HDL-C, LDL-C, triglycerides). Despite the strong evidence supporting frequent testing of LDL-P, its widespread use has been limited due to the costs and limitations of the current assay techniques. Currently the existing methods for measuring LDL-P include nuclear magnetic resonance (NMR), ultracentrifugation and ion mobility—all of which require expensive and bulky instrumentation along with a separate blood sample for analysis. By providing a POC test for LDL-P, the significant portion of the population suffering from LDL-C/LDL-P discordance will have access to comprehensive CVD risk screening thus helping reduce CVD and decrease its associated costs.

SUMMARY

Provided herein, in one aspect, are aptamers with high binding affinity to LDL particles and high selectivity for LDL particles over HDL particles.

In some embodiments, the aptamer is highly selective for L-LDL particles over H-LDL particles.

In some embodiments, the aptamer comprises SEQ. ID NO. 1: ACCTCGATTTTATATTATTTCGCTTAC-CAACAACTGCAGA.

In some embodiments, the aptamer comprises SEQ. ID NO. 2: GTCAGCTTCTTCTATATAATT-CACCTTGCCTCTCGTTCCT.

In some embodiments, the aptamer comprises SEQ. ID NO. 3: AACCTTAATTTACCCTTGTTTTATCATTTCCAT-CATAGCT.

In some embodiments, the aptamer comprises SEQ. ID NO. 4: AAACCATTCTTGTCTCGCATTTTTCTCTTT-TATATTATTT.

In some embodiments, the aptamer comprises SEQ. ID NO. 5: CACGCGCATAACCCTTTTTT-CACCTGCCCTTTTAACTAAT.

In some embodiments, the aptamer comprises SEQ. ID NO. 6: GCCATAAGATGACGACATTCATCACCAAAC-CAACCTCAGC.

In some embodiments, the aptamer comprises SEQ. ID NO. 7: GCCGGGTGATTGAAAAGCAGATTACCGAT-CATCCAATAAA.

In some embodiments, the aptamer consists of SEQ. ID NO. 8: AACTACATGGTATGTGGTGAACTACCTCGAT-TTTATATTATTTCGCTTACCAACAACT GCAGA-GACGTACAATGTACCC.

In some embodiments, the aptamer consists of SEQ. ID NO. 9: AACTACATGGTATGTGGT-GAACTGTCAGCTTCTTCTATATAATT-CACCTTGCCTCTCG TTCCTGACGTACAATGTACCC.

In some embodiments, the aptamer consists of SEQ. ID NO. 10: AACTACATGGTATGTGGTGAACTAACCT-TAATTTACCCTTGTTTTATCATTTCCATCA TAGCTGACGTACAATGTACCC.

In some embodiments, the aptamer consists of SEQ. ID NO. 11: AACTACATGGTATGTGGTGAACTAAACCAT-TCTTGTCTCGCATTTTTCTCTTTTATAT TAT-TTGACGTACAATGTACCC.

In some embodiments, the aptamer consists of SEQ. ID NO. 12: AACTACATGGTATGTGGTGAACTCACGCG-CATAACCCTTTTTTCACCTGCCCTTTTAA CTAATGACGTACAATGTACCC.

In some embodiments, the aptamer consists of SEQ. ID NO. 13: AACTACATGGTATGTGGTGAACTGCCATAA-GATGACGACATTCATCACCAAACCAA CCTCAGCGACGTACAATGTACCC.

In some embodiments, the aptamer consists of SEQ. ID NO. 14: AACTACATGGTATGTGGTGAACTGCCGGGT-GATTGAAAAGCAGATTACCGATCATCC AATAAA-GACGTACAATGTACCC.

Further provided are reagents comprising an aptamer as disclosed herein.

Also provided is a kit comprising an aptamer as disclosed herein.

In another aspect, the disclosure provides a system comprising a plurality of aptamers, wherein the aptamers have a high affinity to LDL particles and high selectivity for LDL particles over HDL particles.

In some embodiments, the plurality of aptamers is immobilized onto a surface.

In some embodiments, a plurality of antisense oligonucleotides is immobilized onto a surface and the plurality of aptamers is annealed to the plurality of antisense oligonucleotides.

In some embodiments, the surface is a gold-, carbon-, or silicon-containing chip.

In some embodiments, the chip is coated with a gold-containing film.

In some embodiments, the film is patterned.

In some embodiments, the film has a thickness of between about 0.2 mm and 2 mm.

In some embodiments, the plurality of aptamers is highly selective for L-LDL particles over H-LDL particles.

In some embodiments, the plurality of aptamers comprises SEQ. ID NO. 1.

In some embodiments, the plurality of aptamers comprises SEQ. ID NO. 2.

In some embodiments, the plurality of aptamers comprises SEQ. ID NO. 3.

In some embodiments, the plurality of aptamers comprises SEQ. ID NO. 4.

In some embodiments, the plurality of aptamers comprises SEQ. ID NO. 5.

In some embodiments, the plurality of aptamers comprises SEQ. ID NO. 6.

In some embodiments, the plurality of aptamers comprises SEQ. ID NO. 7.

In some embodiments, the plurality of aptamers comprises SEQ. ID NO. 8.

In some embodiments, the plurality of aptamers comprises SEQ. ID NO. 9.

In some embodiments, the plurality of aptamers comprises SEQ. ID NO. 10.

In some embodiments, the plurality of aptamers comprises SEQ. ID NO. 11.

In some embodiments, the plurality of aptamers comprises SEQ. ID NO. 12.

In some embodiments, the plurality of aptamers comprises SEQ. ID NO. 13.

In some embodiments, the plurality of aptamers comprises SEQ. ID NO. 14.

In another aspect, the disclosure provides methods of detecting, identifying, and/or quantifying the concentration of lipoprotein particles in a sample, comprising exposing the sample to an aptamer or a plurality of aptamers as disclosed herein, measuring the signal generated by the sample, and analyzing the signal to quantify the concentration of lipoprotein particles in the sample, wherein the signal changes in proportion to the concentration of lipoprotein particles.

In some embodiments, the aptamer or plurality of aptamers selectively binds to LDL particles in the presence of HDL particles.

In some embodiments, the aptamer or plurality of aptamers selectively binds to L-LDL particles in the presence of H-LDL particles.

In some embodiments, the aptamer or plurality of aptamers is attached to a surface.

In some embodiments, the surface is a gold chip.

In some embodiments, the sample comprises blood serum, whole blood, nasal aspirates, saliva, urine, feces, cell lysate, dialysis sampling, tissue biopsy, cell media, or a combination thereof.

In some embodiments, the sample comprises blood serum.

In some embodiments, the sample contains low-density lipoprotein (LDL) and high-density lipoprotein (HDL) particles.

In some embodiments, the bound lipoprotein particle is an LDL particle.

In some embodiments, the LDL particle is an H-LDL particle.

In some embodiments, the LDL particle is an L-LDL particle.

In another aspect, the disclosure provides a method of modulating the activity of a protein in a cell, comprising contacting the protein with the aptamer, reagent, or kit disclosed herein.

In another aspect, the disclosure provides a method of treating or preventing a disease or disorder in a mammal, comprising administering to the mammal the aptamer, reagent, or kit disclosed herein.

DETAILED DESCRIPTION

Definitions

Figure 1:
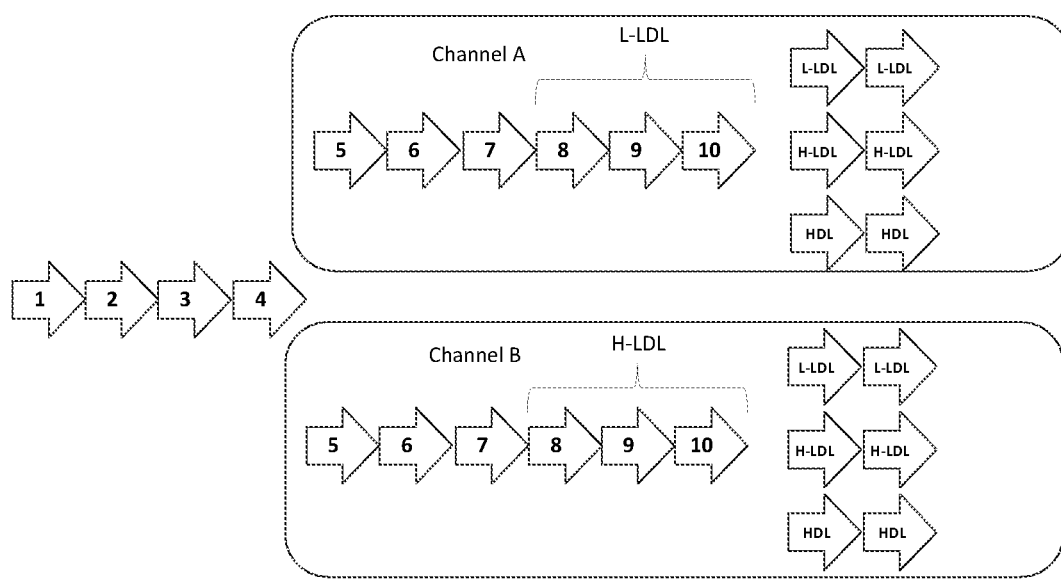
FIG. 1 shows a schematic representation of the aptamer selection process.
Figure 2:
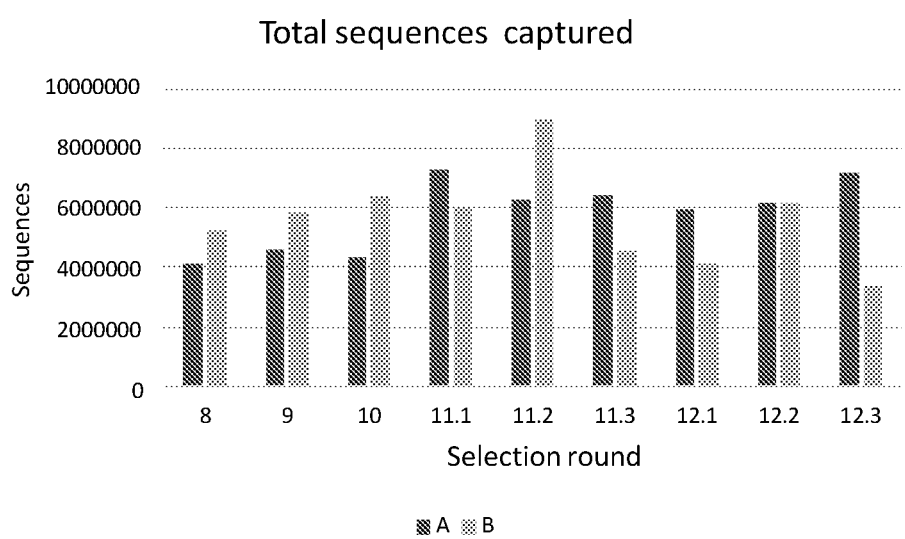
FIG. 2 shows the number of nucleotide sequences captured during rounds 8-12 of the selection process described in FIG. 1.
Figure 3A:
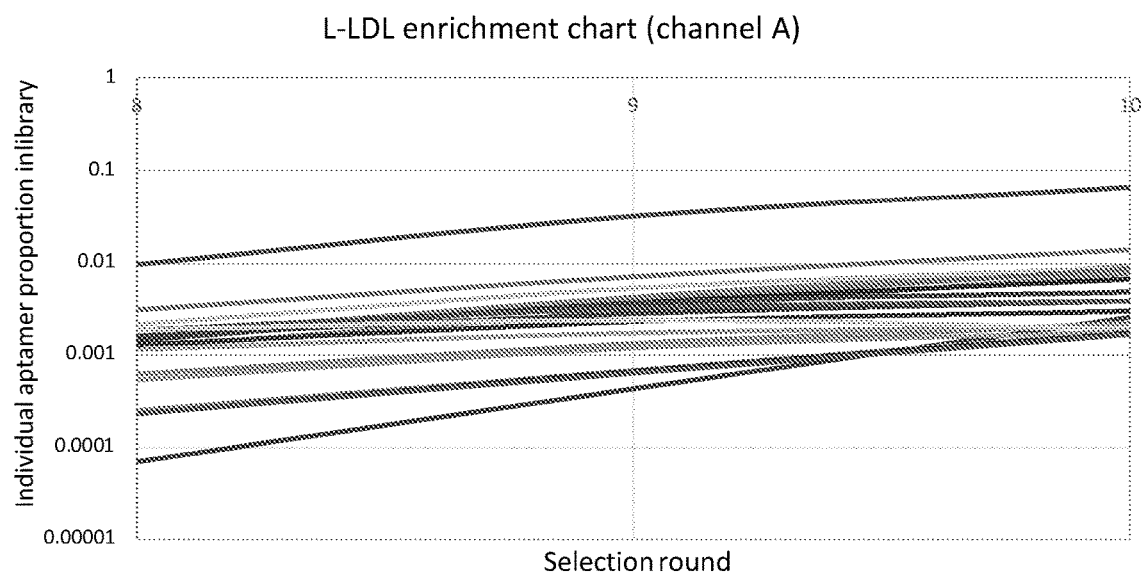
FIG. 3A shows the rate of L-LDL particle enrichment effected by the top 20 sequences during selection rounds 8-10 in Channel A. Channel A is depicted in the upper region of FIG. 1.
Figure 3B:
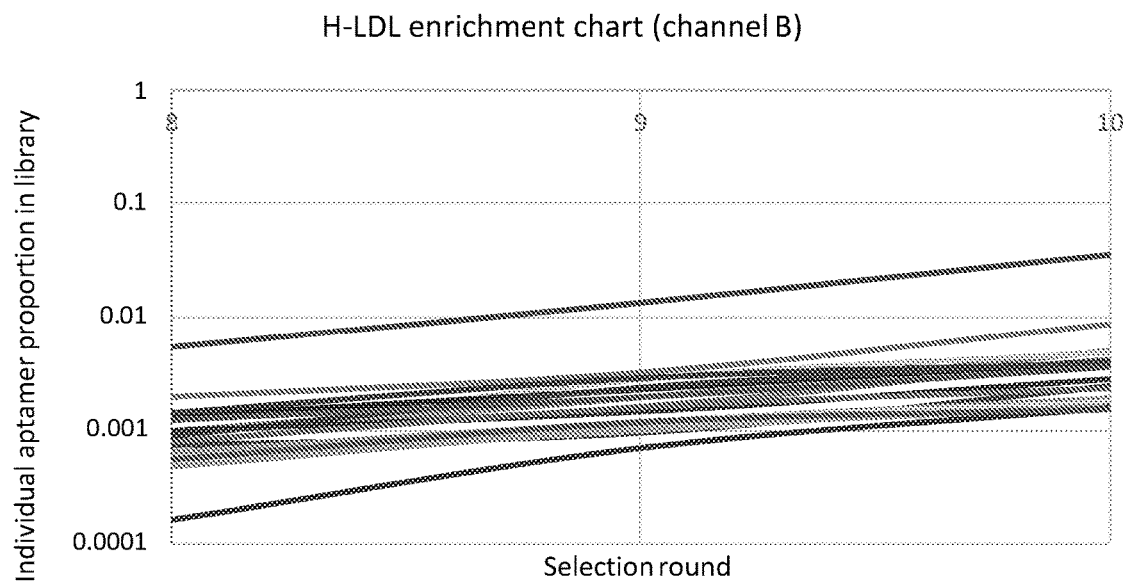
FIG. 3B shows the rate of H-LDL particle enrichment effected by the top 20 sequences during selection rounds 8-10 in Channel B. Channel B is depicted in the lower region of FIG. 1.
Figure 4A:
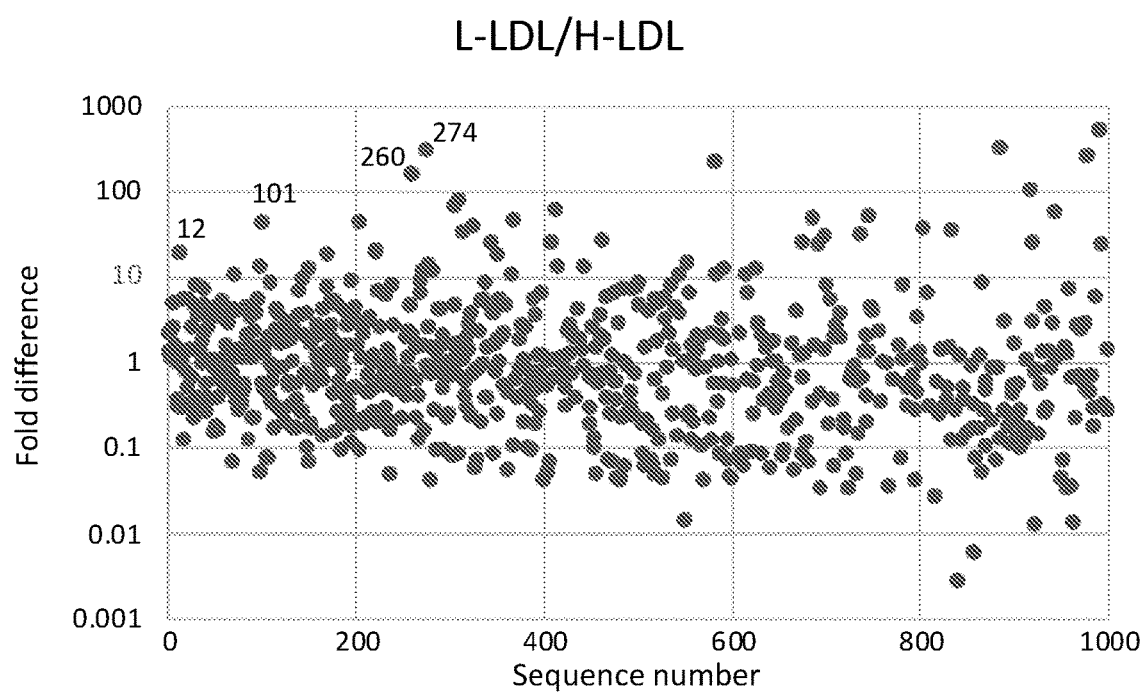
FIG. 4A shows the ratio of selection by L-LDL particles to selection by H-LDL particles for the top 1000 sequences during selection round 12 in Channel A.
Figure 4B:
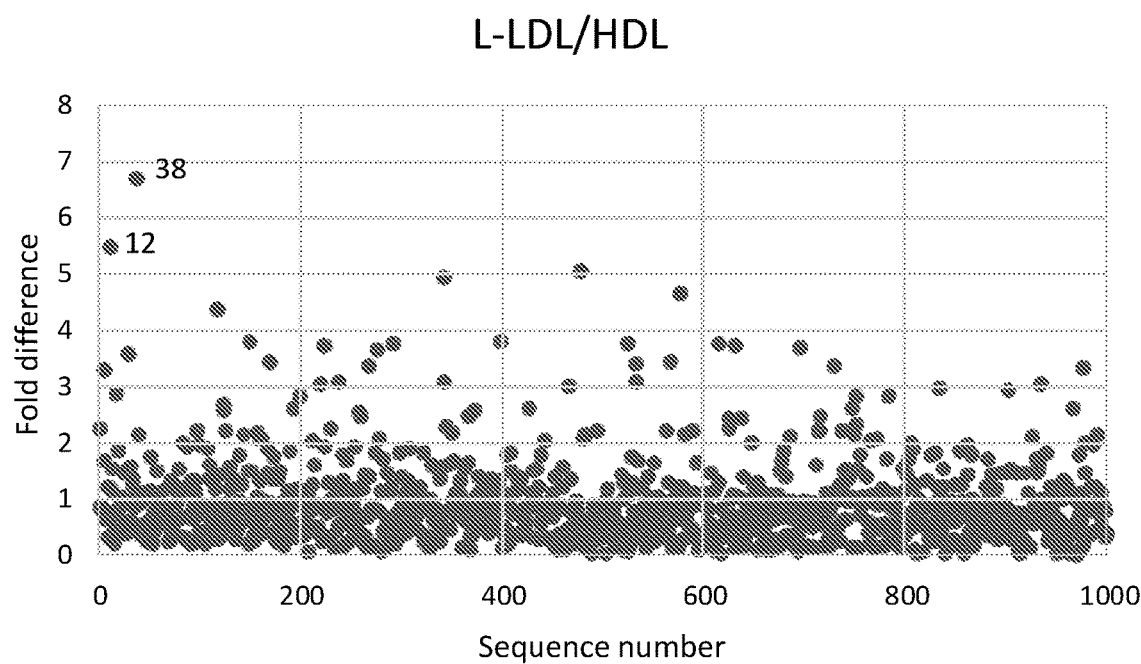
FIG. 4B shows the ratio of selection by H-LDL particles to selection by HDL for the top 1000 sequences during selection round 12 in Channel A.
Figure 5A:
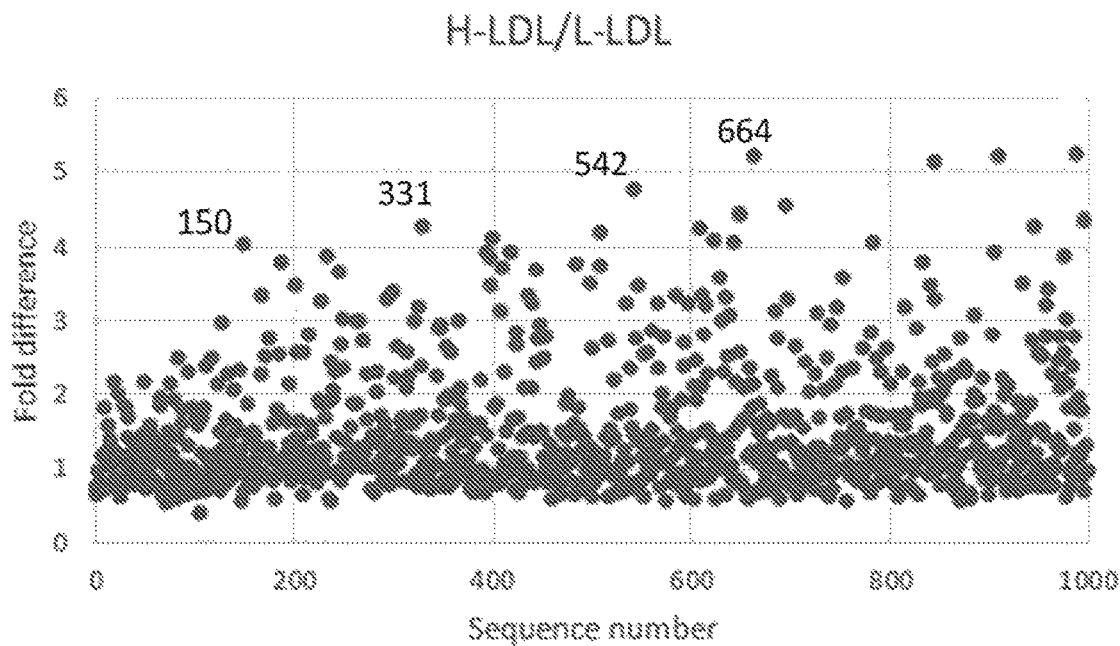
FIG. 5A shows the ratio of selection by H-LDL particles to selection by L-LDL particles for the top 1000 sequences during selection round 12 in Channel A.
Figure 5B:
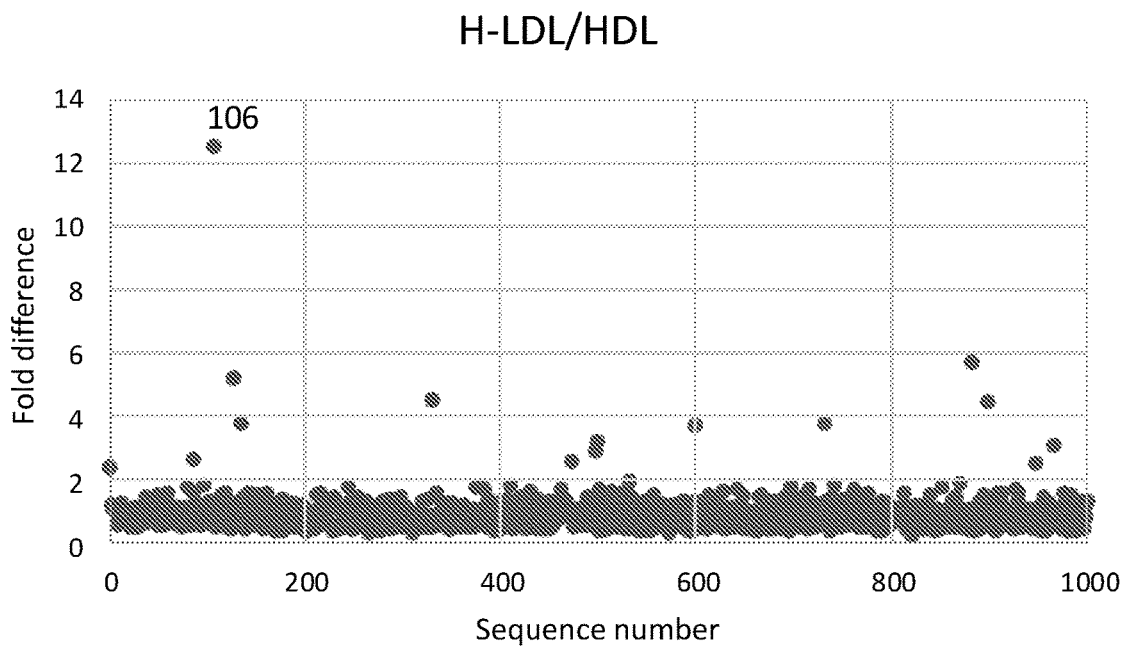
FIG. 5B shows the ratio of selection by H-LDL particles to selection by HDL particles for the top 1000 sequences during selection round 12 in Channel A.

The use of the terms "a," "an," "the," and similar referents in the context of describing the compounds (especially in the context of the claims) are to be construed to cover both the singular and the plural, unless otherwise indicated. It will be further understood that the terms "comprises" and/or "comprising," when used in this specification, specify the presence of stated features, steps, operations, elements and/or components, but do not preclude the presence or addition of one or more other features, steps, operations, elements, components, and/or groups thereof. Recitation of ranges of values herein merely are intended to serve as a shorthand method of referring individually to each separate value falling within the range, unless otherwise indicated herein, and each separate value is incorporated into the specification as if it were individually recited herein. The use of any and all examples, or exemplary language (e.g., "such as") provided herein, is intended to better illustrate the disclosure and is not a limitation on the scope of the disclosure unless otherwise claimed. No language in the specification should be construed as indicating any non-claimed element as essential to the practice of the disclosure.

The terms "LDL particles" or "low density lipoprotein particles" can include particles whose diameters range from about 15 nm to about 23 nm. LDL particles found in plasma can also have a mass of about three million daltons. LDL particles comprise a highly hydrophobic core of approximately 1500 cholesteryl ester molecules surrounded by a shell of phospholipids, unesterified cholesterol, and a single apo-B100 protein. LDL is often differentiated and separated from other plasma lipoproteins by its density of 1.019 to 1.063 g/ml through ultracentrifugation. As used herein, the term "LDL" embraces lipoprotein particles comprising a mutant apo-B100 protein, as well as lipids which do not naturally occur in LDL and labels, all of which may change the physical properties listed above. In all cases an LDL particle contains only one apolipoprotein, an apo-B100 protein or fragment thereof, and contains a lipid core which is predominantly cholesteryl ester.

The term "small LDL particles" or "H-LDL particle" can include particles in the very small (between about 15 and about 18 nm) and intermediate small (between about 18 and about 21 nm) diameter ranges. The term "large LDL particles" or "L-LDL particle" can include particles ranging in diameter between about 21 and about 23 nm. Intermediate sized small particles may be parsed into one of the small and/or large designations or be measured separately as including particles in a size range that is typically near about 20.5 nm. It is noted that the LDL subclasses of particles can be divided in other size ranges. For example, small may be between about 18-20 nm, intermediate may be between about 20-21 nm, and large may be between about 21-23 nm. In addition, intermediate-density lipoprotein particles ("IDL" or "IDL-P"), which range in diameter from approximately 23.0-27.0 nm, can be included among the particles defined as LDL.

The term "HDL particles" or "high-density lipoprotein particles" can include HDL subclasses of particles whose diameters range from between about 7 to about 15 nm. For example, HDL can include particles whose diameters range from between about 8.8 to about 13 nm.

The term "LDL-C" refers to the cholesterol associated with LDL particles.

The term "HDL-C" refers to the cholesterol associated with HDL particles.

As used herein, the term "aptamer" refers to polypeptides or nucleic acids that bind to various molecules such as proteins and hormones. The term lipoprotein particle aptamer or aptamer against lipoprotein particles refers to nucleic acids that bind to lipoprotein particles. Aptamers may be RNA or DNA; there are no particular limitations to the RNA and DNA as long as it binds to lipoprotein particles. Nucleic acids, whose ribose, phosphate backbone, nucleic acid base, and/or 5' and/or 3' end has been modified, may be included in said RNA and DNA, and; there is no limitation as long as these nucleic acids bind to lipoprotein particles. The nucleic acid chain may be single- or double-stranded.

There is no limitation to the length of the aptamer, as long as it is long enough to bind specifically to the lipoprotein particle; however, they may consist of 10 to 200 nucleotides, 10 to 100 nucleotides, 15 to 80 nucleotides, or 15 to 50 nucleotides.

Aptamers comprising nucleotides alone can be used to bind to lipoprotein particles, and also those bound to other molecules, such as polyethylene glycol, cholesterol, peptides, liposome, fluorescent pigments, radioactive substance, toxin or another aptamer, can be used. As used herein, the term "aptamer" includes such aptamers to which other molecules are bound.

Suitable aptamers can be produced by in vitro selection experiments. Aptamers may be generated from random sequences of nucleotides or amino acids, selectively screened by absorption to molecular antigens or cells, and enriched to purify specific high affinity binding ligands, for example. In solution, aptamers may be unstructured but may fold and enwrap target epitopes providing specific binding recognition. The unique folding of the nucleic acids around the epitope, for example, affords discriminatory intermolecular contacts through hydrogen bonding, electrostatic interaction, stacking, and shape complementarity.

The terms "nucleic acid" and "polynucleotide" are terms that generally refer to a string of at least two base-sugar-phosphate combinations. As used herein, the terms include deoxyribonucleic acid (DNA) and ribonucleic acid (RNA) and generally refer to any polyribonucleotide or polydeoxy-ribonucleotide, which may be unmodified RNA or DNA or modified RNA or DNA. RNA may be in the form of a tRNA (transfer RNA), snRNA (small nuclear RNA), rRNA (ribosomal RNA), mRNA (messenger RNA), anti-sense RNA, RNAi (RNA interference construct), siRNA (short interfering RNA), or ribozymes. Thus, for instance, polynucleotides as used herein refers to, among others, single- and double-stranded DNA, DNA that is a mixture of single- and double-stranded regions, single- and double-stranded RNA, and RNA that is mixture of single- and double-stranded regions, hybrid molecules comprising DNA and RNA that may be single-stranded or, more typically, double-stranded or a mixture of single- and double-stranded regions. The terms "nucleic acid sequence" and "oligonucleotide" also encompasses a nucleic acid and polynucleotide as defined above. The term "DNA molecule" includes nucleic acids/polynucleotides that are made of DNA.

It will be appreciated that a great variety of modifications have been made to DNA and RNA that serve many useful purposes known to those of skill in the art. The term polynucleotide as it is employed herein embraces such chemically, enzymatically or metabolically modified forms of polynucleotides, as well as the chemical forms of DNA and RNA characteristic of viruses and cells, including simple and complex cells, inter alia. For instance, the term polynucleotide includes DNAs or RNAs as described above that contain one or more modified bases. Thus, DNAs or RNAs comprising unusual bases, such as inosine, or modified bases, such as tritylated bases, to name just two examples, are polynucleotides as the term is used herein.

The term also includes PNAs (peptide nucleic acids), phosphorothioates, and other variants of the phosphate backbone of native nucleic acids. Natural nucleic acids have a phosphate backbone, artificial nucleic acids may contain other types of backbones, but contain the same bases. Thus, DNAs or RNAs with backbones modified for stability or for other reasons are "nucleic acids" or "polynucleotides" as that term is intended herein.

As used herein, the term "selective binding" means that the aptamer has an at least two-fold greater affinity for one type of lipoprotein over another, or an at least 100-fold greater binding coefficient with respect to one type of lipoprotein over another. As used herein, the term "highly selective binding" means that the aptamer has an at least four-fold greater affinity for one type of lipoprotein over another, or an at least 300-fold greater binding coefficient with respect to one type of lipoprotein over another.

The term "antisense", as used herein, refers to nucleotide sequences that are at least partially complementary to a specific DNA or RNA sequence. The term "antisense strand" is used in reference to a nucleic acid strand that is complementary to the "sense" strand. Antisense molecules may be produced by any method, including synthesis by ligating the gene(s) of interest in a reverse orientation to a viral promoter which permits the synthesis of a complementary strand. Once introduced into a cell, this transcribed strand combines with natural sequences produced by the cell to form duplexes. These duplexes then block either the further transcription or translation. In this manner, mutant phenotypes may be generated. The designation "negative" is sometimes used in reference to the antisense strand, and "positive" is sometimes used in reference to the sense strand.

Antisense compounds include, but are not limited to, compounds that are oligonucleotides, oligonucleosides, oligonucleotide analogs, oligonucleotide mimetics, and chimeric combinations of these. Consequently, while all antisense compounds are oligomeric compounds, not all oligomeric compounds are antisense compounds. As used herein, the term "antisense oligonucleotide" refers to an antisense compound that is an oligonucleotide.

Unless otherwise defined, all terms (including technical and scientific terms) used herein have the same meaning as commonly understood by one having ordinary skill in the art to which this invention belongs. It will be further understood that terms, such as those defined in commonly used dictionaries, should be interpreted as having a meaning that is consistent with their meaning in the context of the relevant art and the present disclosure and will not be interpreted in an idealized or overly formal sense unless expressly so defined herein.

In describing the invention, it will be understood that a number of techniques and steps are disclosed. Each of these has individual benefit and each can also be used in conjunction with one or more, or in some cases all, of the other disclosed techniques. Accordingly, for the sake of clarity, this description will refrain from repeating every possible combination of the individual steps in an unnecessary fashion. Nevertheless, the specification and claims should be read with the understanding that such combinations are entirely within the scope of the invention and the claims.

A system for measuring LDL-P in biological fluid is discussed herein. In the following description, for purposes of explanation, numerous specific details are set forth in order to provide a thorough understanding of the present disclosure. It will be evident, however, to one with expertise in this area that the present disclosure may be practiced without these specific details.

Lipoprotein Particles

Embodiments of the disclosure classify lipoprotein particles into subclasses grouped by size ranges based on functional/metabolic relatedness as assessed by their correlations with lipid and metabolic variables. The evaluations can measure over a number of discrete subpopulations (sizes) of lipoprotein particles, typically between about 30-80 different size subpopulations (or even more). These discrete sub-populations can be grouped into defined subclasses. The defined subclasses can include a plurality of different subclasses for VLDL, HDL and LDL (and which may include IDL as a separate subclass in the size range between LDL and small VLDL).

HDL particle (HDL-P) sizes typically range (on average) from between about 7 nm to about 15 nm, more typically about 7.3 nm to about 14 nm. The HDL subclasses of different size can be quantified from the amplitudes of their spectroscopically distinct lipid methyl group NMR signals. See, Jeyarajah et al., *Lipoprotein particle analysis by nuclear magnetic resonance spectroscopy*, Clin Lab Med. 2006; 26: pp. 847-870, the contents of which are hereby incorporated by reference as if recited in full herein. The HDL-P concentration is the sum of the particle concentrations of all of the respective HDL subpopulations. The NMR derived HDL-P and LDL-P particle sizes noted herein typically refer to average measurements, but other size demarcations may be used. It is contemplated that the defined estimated ranges for one or more of the estimated diameters of the different subpopulations may vary by +/−0.1 nm or somewhat more, particularly when measured with alternative NMR deconvolution protocols or other methods.

It is also noted that while NMR measurements of the lipoprotein particles are contemplated as being particularly suitable for the analyses described herein, it is contemplated that other technologies may be used to measure these parameters now or in the future and embodiments of the invention are not limited to this measurement methodology. Also, other NMR protocols including other NMR deconvolution protocols from those described herein may also be used. See, e.g., Kaess et al., The lipoprotein sub-fraction profile: heritability and identification of quantitative trait loci, J. of Lipid Res. Vol. 49 pp. 715-723 (2008); and Suna et al., 1H NMR metabolomics of plasma lipoprotein sub-classes: elucidation of metabolic clustering by self-organizing maps, NMR Biomed. 2007; 20: 658-672. Examples of non-NMR methods include, for example, flotation and ultra-centrifugation employing a density-based separation technique for evaluating lipoprotein particles. Ion mobility analysis is a different technology for measuring lipoprotein subclass particle concentrations.

LDL particles are known to carry the so-called "bad" cholesterol. LDL particles come in different sizes. Conventionally, the smaller sizes have been thought to be the most dangerous type in that they were generally thought to be inherently more atherogenic than large particles. See, Sacks et al., *Clinical review 163: Cardiovascular endocrinology: Low density lipoprotein size and cardiovascular disease: a reappraisal*, J. Clin. Endocrinol Metab., 2003; 88: 4525-4532. Presently, LDL particle sizes are characterized as "Pattern A" (large) and "Pattern B" (small). Pattern A can be defined as large average particle sizes which typically includes sizes of between about 20.5-23.0 nm. Pattern B can be defined as smaller average particle sizes between about 18.0-20.5 nm. The LDL-P number can be defined as the sum of the small, large and IDL subclass concentrations.

The small LDL particles can include particles whose sizes range from between about 18.0 to about 20.5 nm. The large LDL particles can include particles ranging in diameter between about 20.5-23.0 nm. It is noted that the LDL subclasses of particles can be divided in other size ranges. For example, small may be between about 18.0-20.5 nm, intermediate may be between about 20.5-21.2 nm, and large may be between about 21.2-23 nm. In addition, intermediate-density lipoprotein particles ("IDL" or "IDL-P"), which range in diameter from approximately 23.0-29.0 nm, can be included among the particles defined as LDL.

Aptamers of the Disclosure

Provided herein is an aptamer with high affinity to LDL particles and high selectivity for LDL particles over HDL particles.

For example, the aptamer is highly selective for L-LDL particles over H-LDL particles. For example, the aptamer binds at least three times more strongly to L-LDL particles than to H-LDL particles. For example, the aptamer binds at least five times more strongly to L-LDL particles than to H-LDL particles. For example, the aptamer binds at least ten times more strongly to L-LDL particles than to H-LDL particles.

For example, the aptamer has an at least 100-fold greater binding coefficient with respect to one type of lipoprotein over another. For example, the aptamer has an at least 300-fold greater binding coefficient with respect to one type of lipoprotein over another. For example, the aptamer has an at least 100-fold greater binding coefficient for L-LDL particles over H-LDL particles. For example, the aptamer has an at least 300-fold greater binding coefficient for L-LDL particles over H-LDL particles. For example, the aptamer has an at least 100-fold greater binding coefficient for H-LDL particles over HDL particles. For example, the aptamer has an at least 300-fold greater binding coefficient for H-LDL particles over HDL particles.

For example, the aptamer comprises SEQ. ID NO. 1: ACCTCGATTTTATATTATTTCGCTTAC-CAACAACTGCAGA. For example, the aptamer comprises SEQ. ID NO. 2: GTCAGCTTCTTCTATATAATT-CACCTTGCCTCTCGTTCCT. For example, the aptamer comprises SEQ. ID NO. 3: AACCTTAATT-TACCCTTGTTTTATCATTTCCATCATAGCT. For example, the aptamer comprises SEQ. ID NO. 4: AAAC-CATTCTTGTCTCGCATTTTTCTCTTTTATATTATTT. For example, the aptamer comprises SEQ. ID NO. 5: CACGCGCATAACCCTTTTTTCACCTGCCCTTT-TAACTAAT. For example, the aptamer comprises SEQ. ID NO. 6: GCCATAAGATGACGACATTCATCACCAAAC-CAACCTCAGC. For example, the aptamer comprises SEQ. ID NO. 7: GCCGGGTGATTGAAAAGCAGATTACCGAT-CATCCAATAAA. For example, the aptamer comprises SEQ. ID NO. 8: AACTACATGGTATGTGGTGAAC-TACCTCGATTTTATATTATTTCGCTTACCAACAACT GCAGAGACGTACAATGTACCC. For example, the aptamer comprises SEQ. ID NO. 9: AACTA-CATGGTATGTGGTGAACTGTCAGCTTCTTC-TATATAATTCACCTTGCCTCTCG TTCCTGACGTA-CAATGTACCC. For example, the aptamer comprises SEQ. ID NO. 10: AACTACATGGTATGTGGTGAACTAACCT-TAATTTACCCTTGTTTTATCATTTCCATCA TAGCTG-ACGTACAATGTACCC. For example, the aptamer comprises SEQ. ID NO. 11: AACTACATGGTATGTGGT-GAACTAAACCATTCTTGTCTCGCATTTTTCTCTTT-TATAT TATTTGACGTACAATGTACCC. For example, the aptamer comprises SEQ. ID NO. 12: AACTA-CATGGTATGTGGTGAACTCACGCGCATAACCCTTT-TTTCACCTGCCCTTTTAA CTAATGACGTACAATGT-ACCC. For example, the aptamer comprises SEQ. ID NO. 13: AACTACATGGTATGTGGTGAACTGCCATAA-GATGACGACATTCATCACCAAACCAA CCTCAGCG-ACGTACAATGTACCC. For example, the aptamer comprises SEQ. ID NO. 14: AACTACATGGTATGTGGT-GAACTGCCGGGTGATTGAAAAGCAGATTACCGAT-CATCC AATAAAGACGTACAATGTACCC.

Aptamers of the disclosure can be selected by conducting successive binding tests on libraries of aptamers against L-LDL, H-LDL, and/or HDL particles. A suitable selection method can comprise 1) determining binding coefficients of aptamer libraries against L-LDL, H-LDL, and HDL particles in one vessel, over one or more rounds, and removing the aptamers that exhibit a binding coefficient below a chosen threshold; 2) splitting the library of aptamers into two separate vessels, testing one batch for affinity to L-LDL and the other batch for affinity to H-LDL particles, over one or more rounds, and removing the aptamers that exhibit a binding coefficient below a chosen threshold; 3) determining the binding coefficient of both batches of aptamers, over one or more rounds, against purified samples of L-LDL, H-LDL, and/or HDL particles; and 4) selecting the top aptamers for the libraries can be synthesized using known methods or purchased from commercial vendors.

Lipoprotein Detection System

Provided herein is a system comprising a plurality of aptamers, wherein the aptamers have a high affinity to LDL particles and high selectivity for LDL particles over HDL particles.

For example, the plurality of aptamers is immobilized onto a surface. For example, a plurality of antisense oligonucleotides is immobilized onto a surface and the plurality of aptamers is annealed to the plurality of oligonucleotides.

For example, the surface is a gold-, carbon-, or silicon-containing chip. For example, the surface is a gold chip. For example, the surface is a silica chip. For example, the surface is a glassy carbon chip.

For example, the chip is coated with a gold-containing film. For example, the chip is coated with a silver-containing film. For example, the chip is coated with a platinum-containing film.

For example, the film can be patterned. Suitable methods for patterning include photolithography over one or more steps. For example, the thickness of the film can be 20-100 nm For example, the aptamer is highly selective for L-LDL particles over H-LDL particles. For example, the aptamer binds at least three times more strongly to L-LDL particles than to H-LDL particles. For example, the aptamer binds at least five times more strongly to L-LDL particles than to H-LDL particles. For example, the aptamer binds at least ten times more strongly to L-LDL particles than to H-LDL particles.

For example, the aptamer comprises SEQ. ID NO. 1. For example, the aptamer comprises SEQ. ID NO. 2. For example, the aptamer comprises SEQ. ID NO. 3. For example, the aptamer comprises SEQ. ID NO. 4. For example, the aptamer comprises SEQ. ID NO. 5. For example, the aptamer comprises SEQ. ID NO. 6. For example, the aptamer comprises SEQ. ID NO. 7. For example, the aptamer comprises SEQ. ID NO. 8. For example, the aptamer comprises SEQ. ID NO. 9. For example, the aptamer comprises SEQ. ID NO. 10. For example, the aptamer comprises SEQ. ID NO. 11. For example, the aptamer comprises SEQ. ID NO. 12. For example, the aptamer comprises SEQ. ID NO. 13. For example, the aptamer comprises SEQ. ID NO. 14.

The system may further comprise an electrochemical biosensor for measuring LDL-P as comprising a counter electrode, a working electrode(s), and a reference electrode. These are standard components of electrochemical biosensors and are connected to a potentiostat for measuring the signal that corresponds to the analyte concentration. The electroactive surface area of the biosensor can comprise an Ag/AgCl reference electrode, a nanostructured carbon or gold working electrode, a carbon or platinum counter electrode, and a flexible polyethylene terephthalate (PET) substrate. Additionally, this electrode surface area can be coated with the aptamer or plurality of aptamers selected for lipoprotein particle binding. Unlike traditional methods based on NMR, ultracentrifugation and ion mobility, this method uses lipoprotein particle aptamers to perform electrochemical detection of nanopore blockage, steric hindrance, proximity effects, and/or structure switching properties correlated with lipoprotein particle concentration. There are no specific limitations to the electrode pattern as long as it is made of materials that allow electrochemical reactions, such as platinum, gold, silver, and carbon-based materials such as glass and graphite. For example, the thickness of the electrode can be 100-1000 nm. For example, the thickness of the electrode can be 300-800 nm.

The potentiostat connected to the biochemical sensor for measuring signals generated from the samples can be a circuit that removes capacitive (non-Faradaic) current, allowing higher sensitivities of detection to be achieved. The potentiostat can comprise two current-to-voltage converter circuits connected to two working electrodes (one of which is a control electrode). Said circuits connect directly to a differential amplifier circuit which is then connected to an analog-to-digital converter. This arrangement allows removal of capacitive current in pulse voltammetry before the signal is amplified1 effectively reducing "noise" and allowing signal to be detected at lower target amounts (i.e. enhanced sensitivity).

Methods of Use

Provided herein is a method of detecting, identifying, and/or quantifying lipoprotein particles in a sample, comprising exposing the sample to an aptamer or a plurality of aptamers as disclosed herein, measuring the signal generated by the sample, and analyzing the signal to quantify the concentration of lipoprotein particles in the sample, wherein the signal changes (e.g., increases or decreases) in proportion to the concentration of lipoprotein particles. For example, the method can be used in a basic research laboratory to detect, quantify, or identify lipoprotein particles. For example, the method can be used in a clinical laboratory to detect, quantify, and/or identify lipoprotein particles as biomarkers of disease. For example, the method can be used at the point-of-care (POC) to detect, quantify, and/or identify lipoprotein particles as biomarkers of disease.

For example, the aptamer or plurality of aptamers selectively binds to L-LDL particles in the presence of H-LDL particles. For example, the aptamer or plurality of aptamers has an at least three-fold greater affinity to L-LDL particles relative to H-LDL particles. For example, the aptamer or plurality of aptamers has an at least five-fold greater affinity to L-LDL particles relative to H-LDL. For example, the aptamer or plurality of aptamers has an at least ten-fold greater affinity to L-LDL particles relative to H-LDL particles. For example, the aptamer or plurality of aptamers selectively binds to LDL particles in the presence of HDL particles. For example, the aptamer or plurality of aptamers has an at least three-fold greater affinity to LDL particles relative to HDL particles. For example, the aptamer or plurality of aptamers has an at least five-fold greater affinity to LDL particles relative to HDL. For example, the aptamer or plurality of aptamers has an at least ten-fold greater affinity to LDL particles relative to HDL particles.

For example, the aptamer or plurality of aptamers has an at least 100-fold greater binding coefficient with respect to one type of lipoprotein over another. For example, the aptamer or plurality of aptamers has an at least 300-fold greater binding coefficient with respect to one type of lipoprotein over another. For example, the aptamer or plurality of aptamers has an at least 100-fold greater binding coefficient for L-LDL particles over H-LDL particles. For example, the aptamer or plurality of aptamers has an at least 300-fold greater binding coefficient for L-LDL particles over H-LDL particles. For example, the aptamer or plurality of aptamers has an at least 100-fold greater binding coefficient for LDL particles over HDL particles. For example, the aptamer or plurality of aptamers has an at least 300-fold greater binding coefficient for LDL particles over HDL particles.

For example, the aptamer or plurality of aptamers selectively binds to L-LDL particles in the presence of H-LDL particles. For example, the aptamer or plurality of aptamers has a three-fold greater affinity to L-LDL particles relative to H-LDL particles. For example, the aptamer or plurality of aptamers has a five-fold greater affinity to L-LDL particles relative to H-LDL particles. For example, the aptamer or plurality of aptamers has a ten-fold greater affinity to L-LDL particles relative to H-LDL particles.

For example, the aptamer or plurality of aptamers is immobilized onto a surface. For example, the aptamer or plurality of aptamers is immobilized onto a surface through a disulfide bond.

For example, the surface is a gold chip. In some embodiment, the surface is a gold-coated surface. For example, the surface is a silica surface. For example, the surface is a glassy carbon surface.

Suitable samples include, but are not limited to, biological samples selected from the group consisting of: blood serum, whole blood, nasal aspirates, saliva, urine, feces, cell lysate, dialysis sampling, tissue biopsy, cell media, and a combination thereof. For example, the biological sample is unprocessed. For example, the whole blood, saliva, or urine samples have not been processed through dilution or purification steps.

For example, the sample contains LDL particles and HDL particles.

For example, the bound lipoprotein particle is an LDL particle.

For example, the LDL particle is an H-LDL particle.

For example, the LDL particle is an L-LDL particle.

In a method for comparing specific binding capacities of an aptamer specifically bound to a lipoprotein with respect to other lipoproteins and magnitudes of binding force depending on a concentration of the lipoprotein, an NMR or surface plasmonic resonance (SPR) device may be used. To do so, a surface of a chip is modified and each aptamer is immobilized onto the chip. Then, a lipoprotein is contacted thereon at various concentrations and binding force thereof is determined and also binding force with respect to other counter-target materials is tested for analyzing specific binding capacities.

The method can include a method of detecting, identifying, and/or quantifying a single molecule of lipoprotein particles or a concentration of lipoprotein particles as low as the attomolar to millimolar range. For example, a concentration of lipoprotein particles in the sample as low as about 1 attomolar is detected. For example, the method is used to detect a single molecule of lipoprotein particles protein or peptide. For example, the method is used to detect femtomolar concentrations of lipoprotein particles. For example, the method is used to detect picomolar concentrations of lipoprotein particles. For example, the method is used to detect nanomolar concentrations of lipoprotein particles. For example, the method is used to detect micromolar concentrations of lipoprotein particles. For example, the method is used to detect millimolar concentrations of lipoprotein particles. Suitable quantification methods include, but are not limited to, using a readout method selected from surface plasmon resonance (SPR), Raman spectroscopy, NMR, and a combination thereof.

Aptamers of the disclosure can be used to modulate the activity of a protein in a cell. For example, the aptamer can be used to activate an inactive protein or enhance the activity of an active protein, i.e., behave as an agonist. For example, the aptamer can be used to inhibit, or attenuate the activity of a protein or deactivate a protein, i.e., behave as an antagonist. For example, the protein can be an enzyme or receptor.

Aptamers of the disclosure can also be used to treat or prevent a disease or disorder in a mammal. For example, the mammal can be a human.

EXAMPLES

Example 1: Analysis of Aptamer Sequences

Next generation sequencing was performed with an Illumina HiSeq instrument at the Hospital for Sick Children (Toronto). Sequences were received by NeoVentures as raw fastq files. NeoVentures software parses the sequences into each library on the basis of hex codes that were inserted immediately upstream of the forward primer recognition site. Sequences were also filtered based on integrity (only 40 nt random regions with matching flanking sequences) and quality (all bases in sequences had to have a base call quality score of 13 or higher).

Between 4 and 9 million sequences were captured per library for a total of slightly more than 100 million sequences. To normalize for variation in the number of sequences observed per library, the copy number observed for each sequence was divided by the total number of sequences observed for that library, and this normalized value was reported as sequence frequency.

FIG. 1 depicts the aptamer selection process. Ten rounds of selection were conducted against purified LDL particles. The purified LDL particles were separated into L-LDL and H-LDL particles by ultracentrifugation as described above. Rounds 1-4 involved the selection of aptamers against both L-LDL and H-LDL particles in one vessel. The aptamer libraries were then split into two channels, A and B. Selection rounds 5-7 involved the selection of aptamers against both L-LDL and H-LDL particles in each channel. Afterwards, Channel A was charged with pure L-LDL particles, Channel B was charged with pure H-LDL particles, and selection rounds 8-10 were conducted as previously described. The remaining libraries in each channel were further split into three groups, and each group underwent selection again L-LDL, H-LDL, and HDL particles, respectively, in rounds 11 and 12. Sequences were named based on their copy number in selection round 10, e.g., sequence LDL-A1 is the sequence with the highest copy number in selection round 10 in channel A. As a result of the analyses described above and depicted in FIGS. 2-5, aptamers A1, A2, A12, A38, A274, B150, and B664 were selected for further analysis of binding to LDL.

Example 2. Analysis of Binding to LDL

The aptamers were synthesized with a disulfide group on the 5' end and spotted onto a gold chip at a concentration of 400 µM in triplicate. Gold reduces the disulfide bond and then oxidizes the remaining thiols in a strong metallic bond. This means that for each aptamer bound to the chip there is also a spacer molecule with the blocking group also bound. The rest of the chip was then blocked with thiolated PEG molecules (550 daltons, at a concentration of 100 µM).

Target molecules are injected at a volume of 200 µL at a flow rate of 10 µL/min. This means that the association phase should last for 20 minutes. In practice, the edge of this phase appears at an earlier time because of diffusion of the target. Magnetic resonance is measured simultaneously on each spot and the average for each aptamer is computed.

The coefficient of disassociation ($k_d$) was determined with the following equation:

$$\frac{dx}{dt} = -k_d * x$$

$k_d$ was then used to compute the coefficient of association ($k_a$) with the following equation:

$$\frac{dx}{dt} = (k_a * R_{max} * c - (k_a * c + k_d)) * x$$

The binding coefficient $k_D$ is defined as the ratio of the dissociation coefficient to the association coefficient:

$$k_D = k_d/k_a$$

Figure 7A:
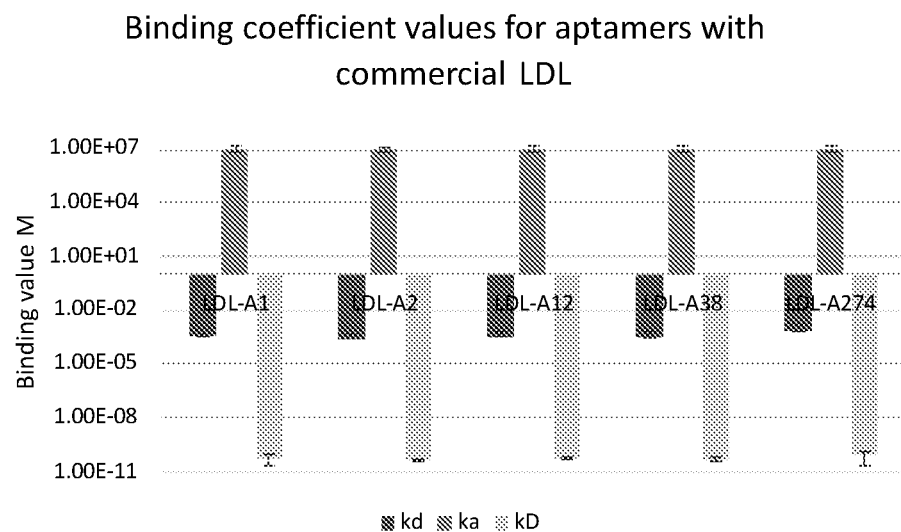
FIG. 7A shows the dissociation coefficient, association coefficient, and binding coefficient for aptamers LDL-A1, LDL-A2, LDL-A12, LDL-A38, and LDL-A274 against a commercial sample of LDL.
Figure 7B:
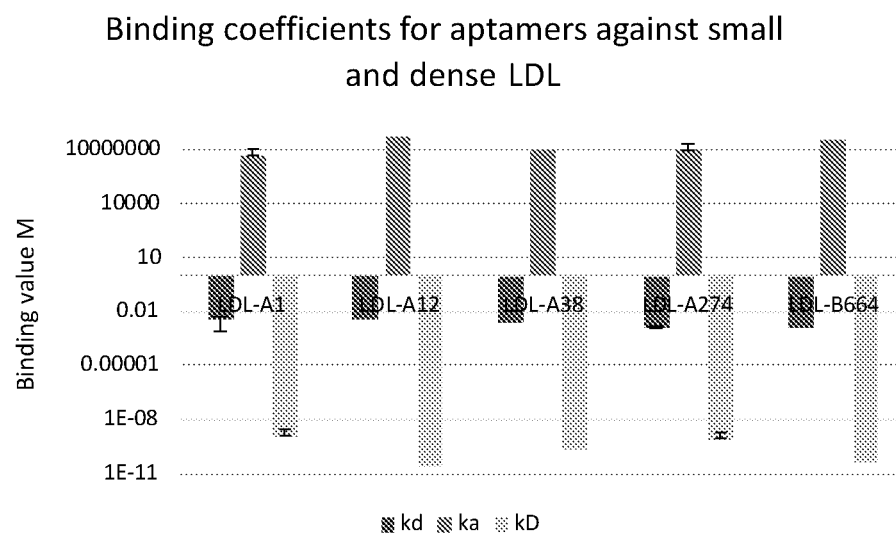
FIG. 7B shows the dissociation coefficient, association coefficient, and binding coefficient for aptamers LDL-A1, LDL-A12, LDL-A38, LDL-A274, and LDL-B664 against pure H-LDL.
Figure 7C:
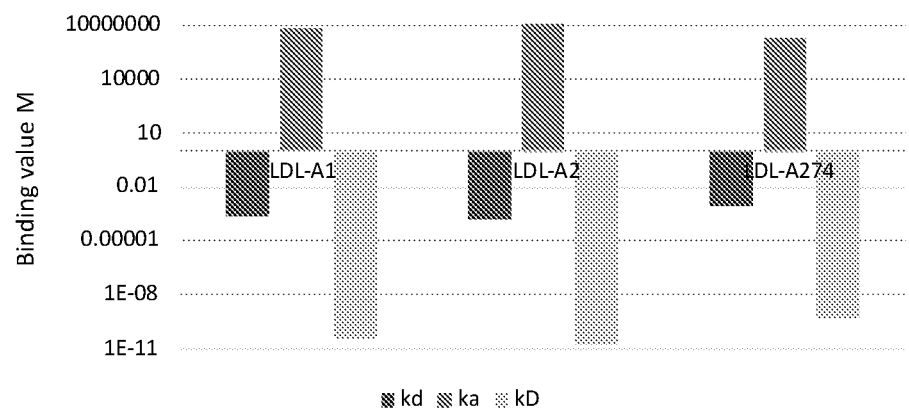
FIG. 7C shows the dissociation coefficient, association coefficient, and binding coefficient for aptamers LDL-A1, LDL-A2, and LDL-A274, against pure L-LDL.

Two different chips were tested with the full set of aptamers. The binding coefficients for all experiments are provided below and in FIGS. 7A-7C.

TABLE 1

Commercial LDL

| | | kd | ka | kD |
|---|---|---|---|---|
| Commercial LDL | LDL-A1 | 3.69E−04 | 6.50E+06 | 5.31E−11 |
| | LDL-A2 | 2.61E−04 | 6.15E+06 | 4.21E−11 |
| | LDL-A12 | 3.35E−04 | 6.58E+06 | 4.97E−11 |
| | LDL-A38 | 3.00E−04 | 6.50E+06 | 4.55E−11 |
| | LDL-A274 | 6.48E−04 | 7.55E+06 | 7.73E−11 |

TABLE 2

H-LDL

| | | kd | ka | kD |
|---|---|---|---|---|
| Small and dense | LDL-A1 | 0.001453 | 4803593 | 1.23E−09 |
| | LDL-A12 | 0.00114 | 49494088 | 2.3E−11 |
| | LDL-A38 | 0.002335 | 9991116 | 2.34E−10 |
| | LDL-A274 | 0.001264 | 9292209 | 7.92E−10 |
| | LDL-B664 | 0.001341 | 32000284 | 4.19E−11 |

TABLE 3

L-LDL

| | | kd | ka | kD |
|---|---|---|---|---|
| Large and fluffy | LDL-A1 | 0.000236 | 7229576 | 3.27E−11 |
| | LDL-A2 | 0.000179 | 11297000 | 1.59E−11 |
| | LDL-A274 | 0.00088 | 1828196 | 4.82E−10 |

Figure 8:
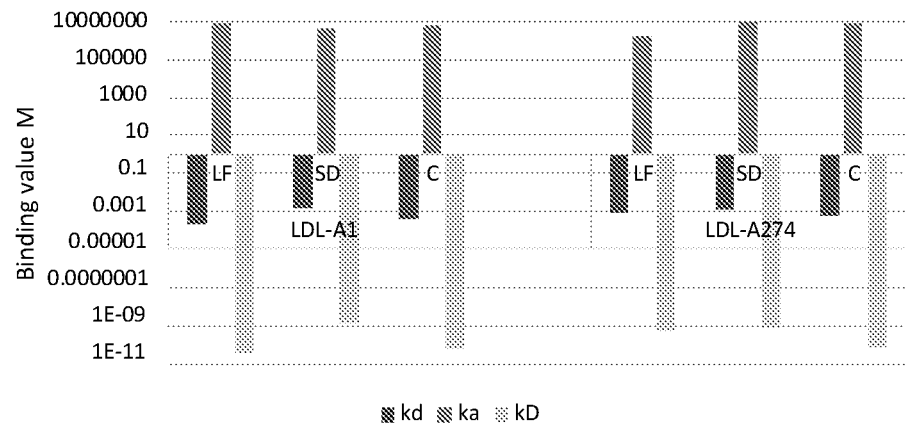
FIG. 8 shows a comparison of dissociation, association, and binding coefficients for LDL-A1 and LDL-A274 against L-LDL, H-LDL, and commercial LDL.

From the data above and in FIG. 8, it appears that the aptamer LDL-A1 binds with higher affinity to L-LDL particles than to H-LDL particles, whereas aptamer LDL-A274 does not exhibit a preference for the type of LDL particle to which it binds.

The binding affinities of these aptamers in blood serum were also measured. A 1% blood serum in Selection Buffer as a base was used as media. First, the gold chip was tested with 1 nM LDL to ensure that the binding coefficients that were measured were the same as previously estimated. Then, 1% blood serum with 1 nM LDL added was tested, as well as pure blood serum. The resonance values observed for blood serum with 1 nM LDL was subtracted from the pure blood serum. The resonance from the negative aptamer was subtracted from these normalized values. The estimated binding coefficients from this procedure are shown in Tables 4 and 5.

TABLE 4

Commercial LDL with gold chip

| | kd | ka | kD |
|---|---|---|---|
| LDL-A274 | 0.000117 | 5474416 | 2.14E−11 |
| LDL-A12 | 7.54E−05 | 7011128 | 1.08E−11 |
| LDL-A2 | 8.99E−05 | 5981547 | 1.5E−11 |

TABLE 4-continued

Commercial LDL with gold chip

| | kd | ka | kD |
|---|---|---|---|
| LDL-A38 | 0.000117 | 5652437 | 2.07E−11 |
| LDL-A1 | 1.31E−05 | 7823166 | 1.68E−12 |

TABLE 5

Commercial LDL in blood serum

| | kd | ka | kD |
|---|---|---|---|
| LDL-A274 | 0.000589 | 5170946 | 1.14E−10 |
| LDL-A12 | 0.000415 | 8899633 | 4.66E−11 |
| LDL-A2 | 5.21E−05 | 10165515 | 5.12E−12 |
| LDL-A38 | 9.09E−05 | 5095581 | 1.78E−11 |

Figure 9:
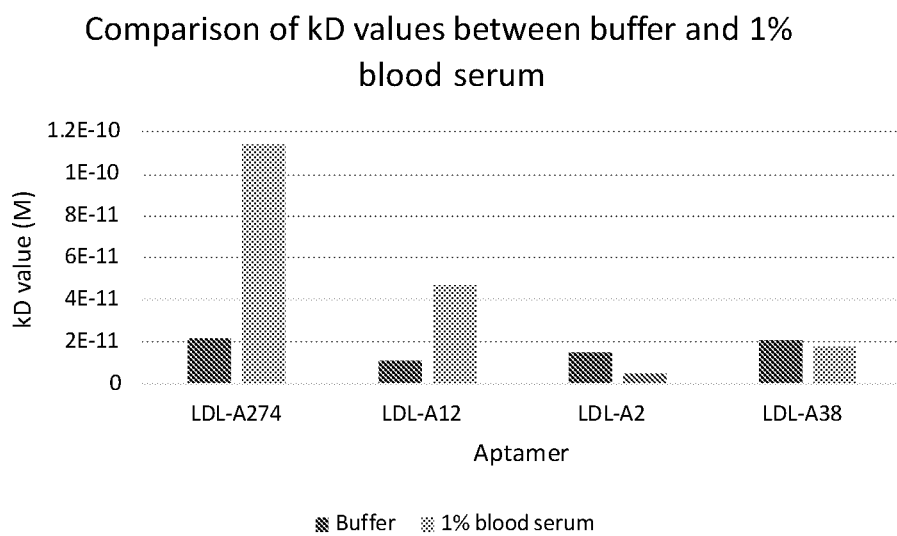
FIG. 9 shows a comparison of binding coefficients in buffer and 1% blood serum for aptamers LDL-A274, LDL-A12, LDL-A-2, and LDL-A38.
Figure 10:
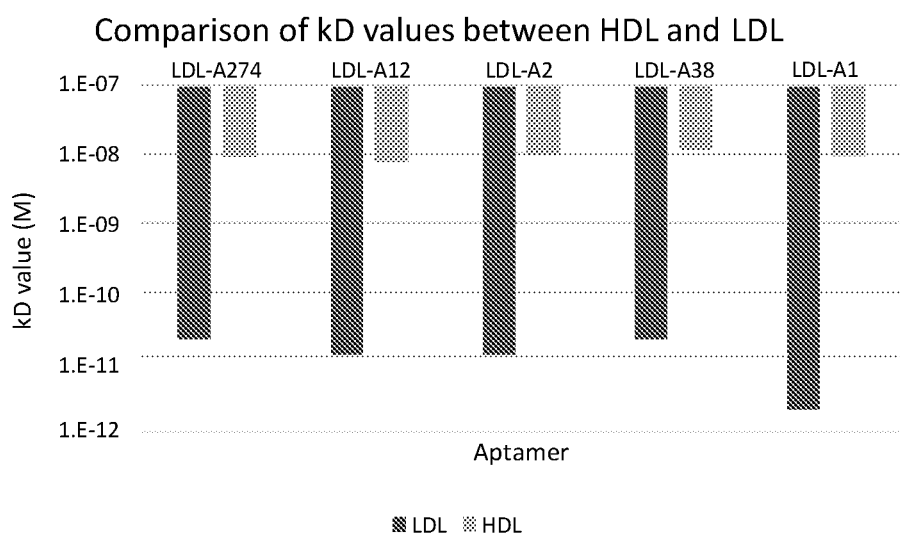
FIG. 10 shows a comparison of binding coefficients against LDL and HDL for aptamers LDL-A274, LDL-A12, LDL-A-2, LDL-A38, and LDL-A1.

FIG. 9 shows a comparison of the $k_D$ values for four of the aptamers in the presence and absence of blood serum. Aptamers LDL-A274 and LDL-A12 both performed less well in blood serum, while aptamers LDL-A2 and LDL-A38 appeared to be unaffected by the medium.

Figure 6A:
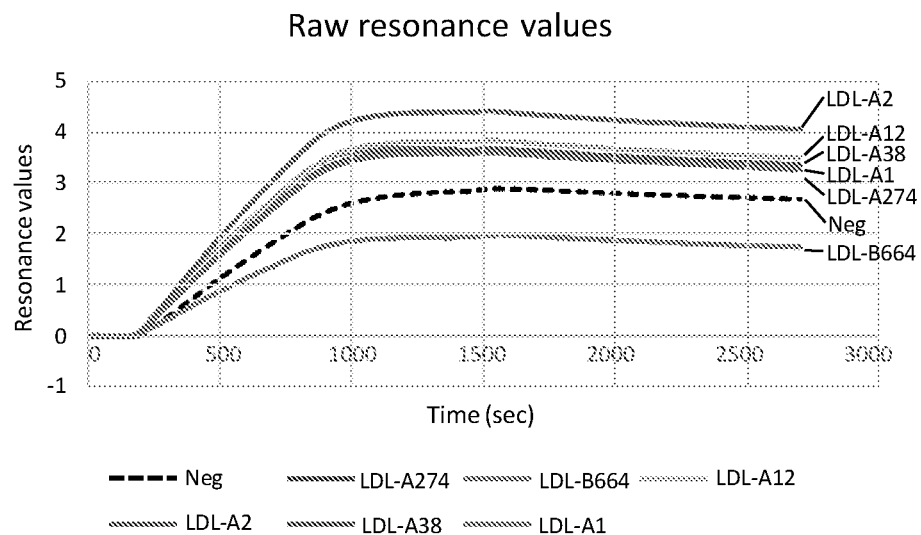
FIG. 6A shows the raw resonance values for a negative aptamer with a random sequence, as well as for LDL-A1, LDL-A2, LDL-A12, LDL-A38, LDL-A274, and LDL-B664, against commercially purchased LDL. Resonance is a measurement of both the flow of the target over the chip and the binding of the target to aptamers.
Figure 6B:
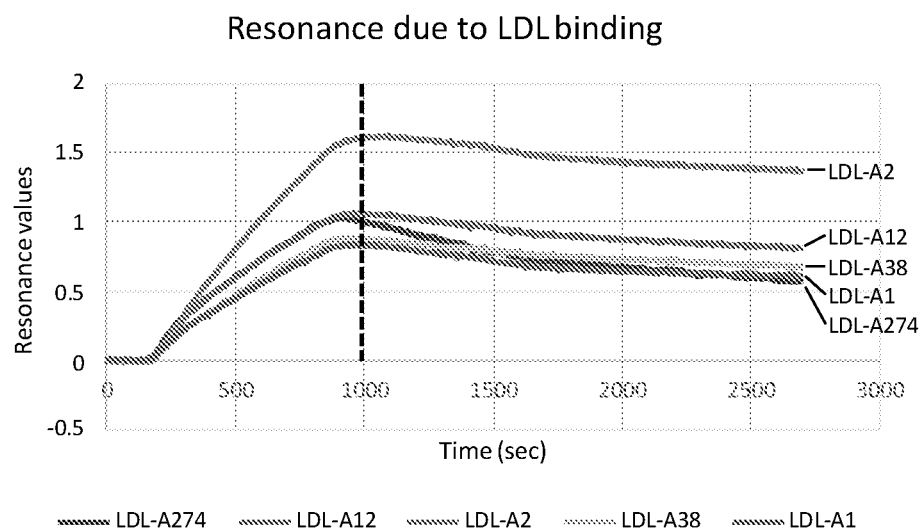
FIG. 6B shows the resonance values due to LDL particle binding, determined by subtracting the resonance of the negative aptamer from that of the aptamer of interest, for LDL-A1, LDL-A2, LDL-A12, LDL-A38, and LDL-A274. Resonance is a measurement of both the flow of the target over the chip and the binding of the target to aptamers.

Finally, HDL was also tested in selection buffer. The HDL signal was much lower than the LDL signal. Therefore, the concentration injected was increased from 1 nM to 100 nM. Table 6 shows the estimated binding coefficients for various aptamers against HDL. FIG. 6 shows comparative data from Tables 4 and 6.

TABLE 6

HDL binding

| | kd | ka | kD |
|---|---|---|---|
| LDL-A274 | 0.000401 | 48575 | 8.26E−09 |
| LDL-A12 | 0.000418 | 57678 | 7.25E−09 |
| LDL-A2 | 0.000567 | 58544 | 9.69E−09 |
| LDL-A38 | 0.000592 | 51391 | 1.15E−08 |
| LDL-A1 | 0.000656 | 72792 | 9.01E−09 |

Example 3. Displacement of Aptamers from Antisense with LDL

The aptamers disclosed herein can be incorporated into a biosensor application for the purpose of electrochemical detection of LDL on a surface. This can be achieved by have the aptamers annealed to shorter antisense constructs that are immobilized on a reactive surface. For this application, it would necessary to identify antisense sequences that can bind to the aptamer, but from which the aptamer is still displaceable by LDL.

Three antisense constructs were designed for the LDL-A1 aptamer, as well as two antisense constructs for each of the LDL-A2 and LDL-A12 aptamers. Their designations and molecular weights are provided below.

| | | |
|---|---|---|
| A: | LDL-A1.1 | MW: 4664.3 Da |
| B: | LDL-A1.2 | MW: 5312.8 Da |
| C: | LDL-A1.3 | MW: 5330.7 Da |
| D: | LDL-A2.1 | MW: 4840.4 Da |
| E: | LDL-A2.2 | MW: 5935.1 Da |
| F: | LDL-A12.1 | MW: 5620 Da |
| G: | LDL-A12.2 | MW: 5330.8 Da |

Each antisense was spotted on a gold chip in triplicate at a concentration of 100 μM and 10 uM. Each aptamer was tested individually. First, each aptamer was injected at a concentration of 1 uM. Without removing the aptamer, LDL was then injected commercial at a concentration of 100 pM. The resonance curves for each injection were measured and analyzed separately. The total observed resonance for each of the three LDL-A1 antisense oligonucleotides, labeled A, B, and C, was determined by averaging three separate immobilized spots, each with a concentration of 100 uM.

Figure 11A:
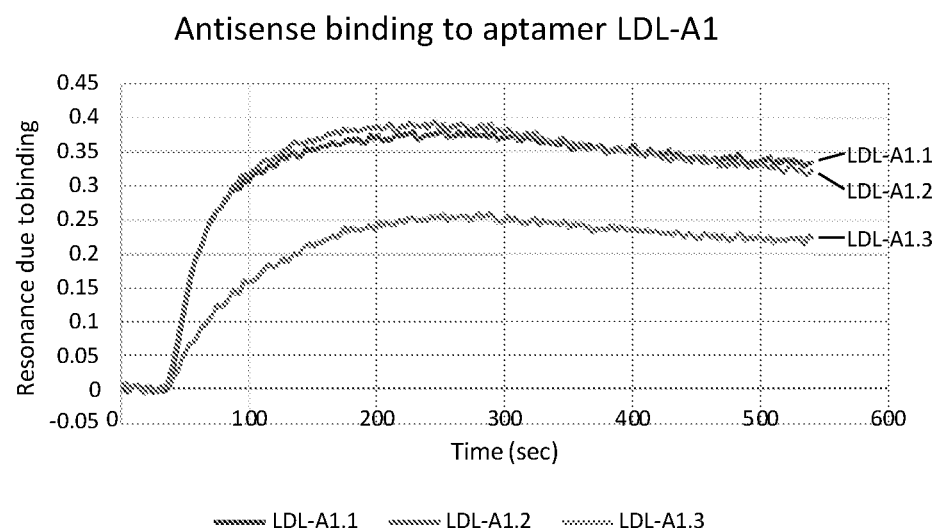
FIG. 11A shows the resonance signals due to binding of antisense oligonucleotides LDL-A1.1, LDL-A1.2, and LDL A1.3 to aptamer LDL-A1.
Figure 11B:
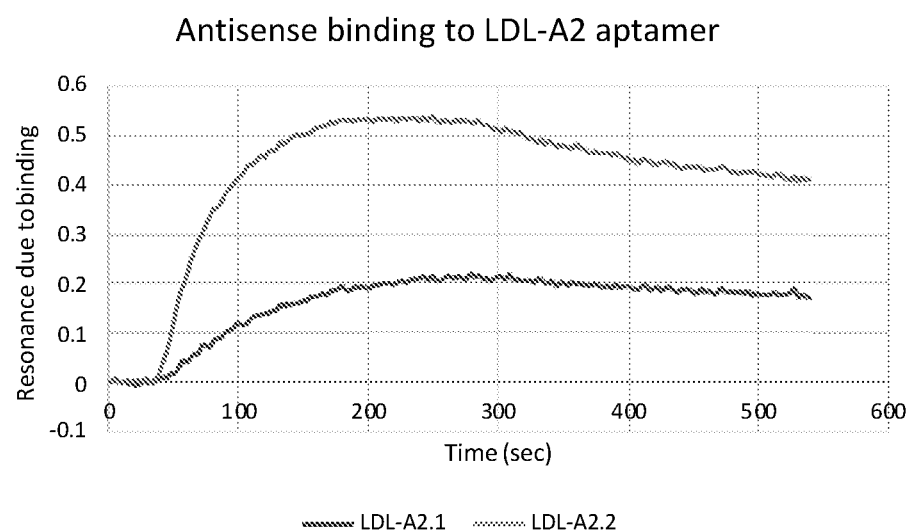
FIG. 11B shows the resonance signals due to binding of antisense oligonucleotides LDL-A2.1 and LDL-A2.2 to aptamer LDL-A2.
Figure 11C:
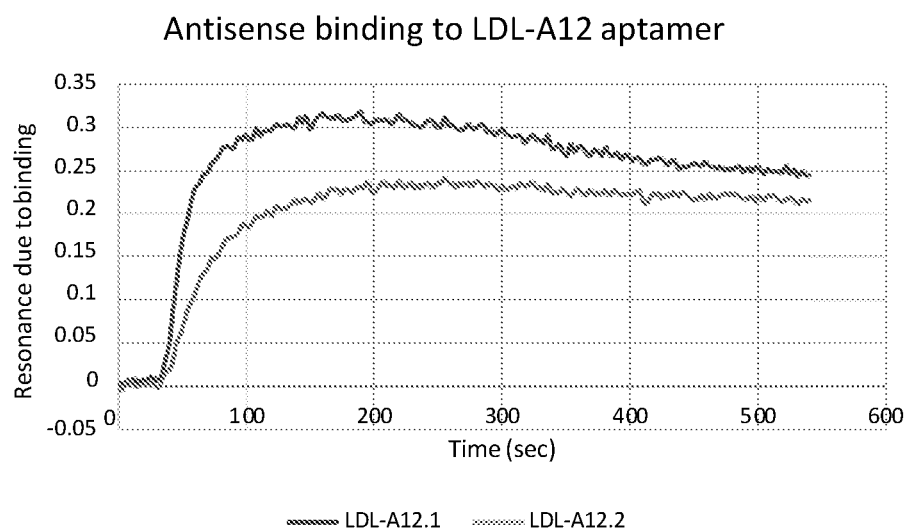
FIG. 11C shows the resonance signals due to binding of antisense oligonucleotides LDL-A12.1 and LDL-A12.2 to aptamer LDL-A12.

FIG. 11A shows the resonance signals due to binding of three different antisense nucleotides to LDL-A1. LDL-A1 injected at a concentration of 1 uM in a volume of 200 uL and a flow rate of 50 uL/min. FIGS. 11B and 11C shows the resonance signals due to binding of several different antisense oligonucleotides to LDL-A2 and LDL-A3, respectively. The binding curve shown in FIG. 11A was determined by subtracting the average total resonance of the four antisense constructs that were not designed to bind to LDL-A1, designated as D, E, F, and G, from respective LDL-A1 antisense oligonucleotides. An analogous process was used to produce the binding curves shown in FIGS. 11B and 11C.

Figure 12A:
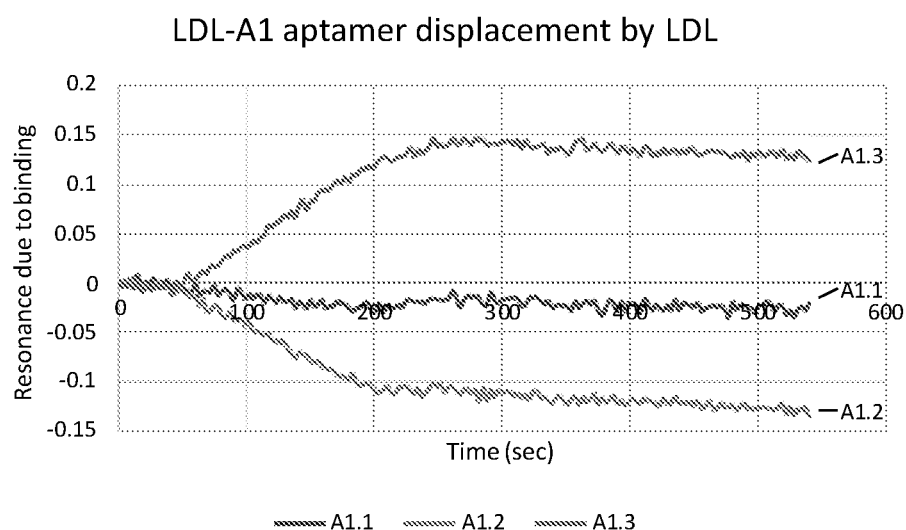
FIG. 12A shows the change in the resonance signal due to binding of antisense oligonucleotides LDL-A1.1, LDL-A1.2, and LDL-A1.3 to aptamer LDL-A1 upon addition of LDL over time.
Figure 12B:
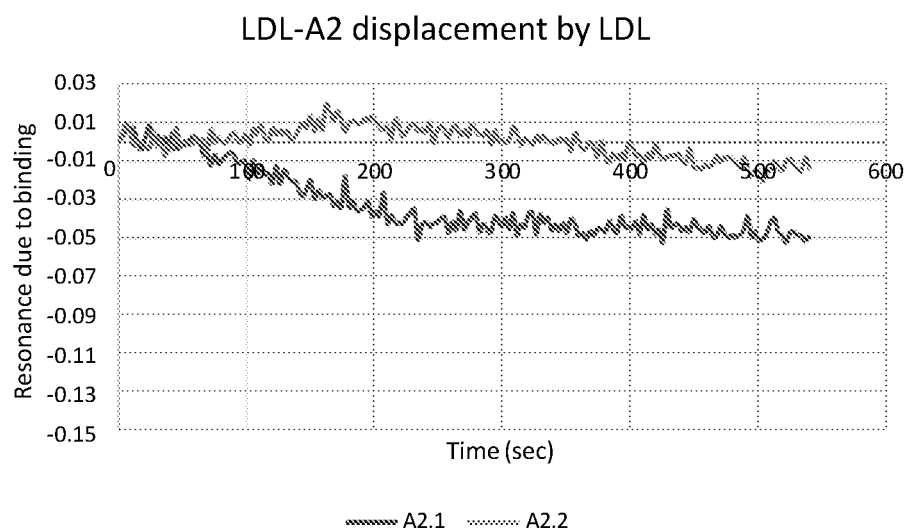
FIG. 12B shows the change in the resonance signals due to binding of antisense oligonucleotides LDL-A2.1 and LDL-A2.2 to aptamer LDL-A2 upon addition of LDL over time.
Figure 12C:
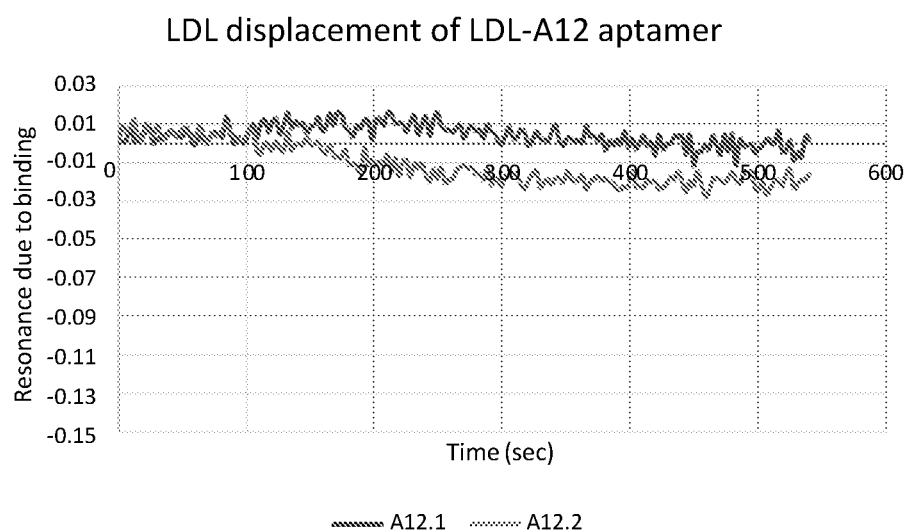
FIG. 12C shows the change in the resonance signals due to binding of antisense oligonucleotides LDL-A12.1 and LDL-A12.2 to aptamer LDL-A12 upon addition of LDL over time.

LDL exhibits a very strong resonance effect in flow. It was determined that the resonance response of LDL in general was negatively correlated with the molecular weight of the antisense constructs. A key exception to this was the LDL-A1.3 antisense. The other antisense spots were used to construct a trend line and to subtract the LDL response in each case from the positive control aptamers. The results of this process are shown in FIGS. 12A-12C.

LDL-A1.3 exhibited an increase in resonance as a result of LDL in flow even after correction with the negative antisense. This result can be interpreted to mean that either the aptamer was able to bind to LDL while hybridized to the antisense, or the antisense itself exhibits some capacity to bind to LDL.

LDL-A1.1 exhibited very weak displacement, while LDL-A1.2 exhibited strong displacement. Note that the aptamer/antisense binding was very similar between these two antisense nucleotides, while the LDL displacement is quite different. For the LDL-A2 aptamer, displacement was clearly observed for the A2.1 antisense but not for A2.2. This was expected as the LDL-A2.1 antisense hybridized less strongly with this aptamer than the LDL-A2.2 antisense. It is clear that neither of the LDL-A12 antisense were displaced effectively by LDL.

The association, dissociation, and binding coefficients for aptamers binding to the above-mentioned LDL-antisense constructs are shown in Table 7.

TABLE 7

| Antisense binding | | | | |
|---|---|---|---|---|
| Aptamer | Antisense | kd | ka | kD |
| LDL-A2 | LDLA2.1 | 2.67E-03 | 3.42E+04 | 7.82E-08 |
|  | LDL-A2.2 | 2.85E-03 | 6.03E+04 | 4.73E-08 |
| LDL-A12 | LDL-A12.1 | 2.85E-03 | 6.03E+04 | 4.73E-08 |
|  | LDL-A12.2 | 1.11E-03 | 6.37E+04 | 1.74E-08 |
|  | LDL-A1.1 | 1.33E-03 | 9.68E+04 | 1.37E-08 |
| LDL-A1 | LDL-A1.2 | 2.01E-03 | 7.40E+04 | 2.71E-08 |
|  | LDL-A1.3 | 1.63E-03 | 4.25E+04 | 3.85E-08 |

EQUIVALENTS

The details of one or more embodiments of the disclosure are set forth in the accompanying description above. Although any methods and materials similar or equivalent to those described herein can be used in the practice or testing of the present disclosure, the preferred methods and materials are now described. Other features, objects, and advantages of the disclosure will be apparent from the description and from the claims. In the specification and the appended claims, the singular forms include plural referents unless the context clearly dictates otherwise. Unless defined otherwise, all technical and scientific terms used herein have the same meaning as commonly understood by one of ordinary skill in the art to which this disclosure belongs. All patents and publications cited in this specification are incorporated by reference.

The foregoing description has been presented only for the purposes of illustration and is not intended to limit the disclosure to the precise form disclosed, but by the claims appended hereto.

What is claimed is:

1. An aptamer with high affinity to LDL particles and high selectivity for LDL particles over HDL particles, wherein the aptamer includes a sequence selected from one of: SEQ. ID NO. 1: ACCTCGATTTTATATTATTTCGCTTACCAACAACTGCAGA; SEQ. ID NO. 2: GTCAGCTTCTTCTATATAATTCACCTTGCCTCTCGTTCCT; SEQ. ID NO. 3: AACCTTAATTTACCCTTGTTTTATCATTTCCATCATAGCT; SEQ. ID NO. 4: AAACCATTCTTGTCTCGCATTTTTCTCTTTTATATTATTT; SEQ. ID NO. 5: CACGCGCATAACCCTTTTTTCACCTGCCCTTTTAACTAAT; SEQ. ID NO. 6: GCCATAAGATGACGACATTCATCACCAAACCAACCTCAGC; SEQ. ID NO. 7: GCCGGGTGATTGAAAAGCAGATTACCGATCATCCAATAAA; SEQ. ID NO. 8: AACTACATGGTATGTGGTGAACTACCTCGATTTTATATTATTTCGCTTACCAACAACT GCAGAGACGTACAATGTACCC; SEQ. ID NO. 9: AACTACATGGTATGTGGTGAACTGTCAGCTTCTTCTATATAATTCACCTTGCCTCTCG TTCCTGACGTACAATGTACCC; SEQ. ID NO. 10: AACTACATGGTATGTGGTGAACTAACCTTAATTTACCCTTGTTTTATCATTTCCATCA TAGCTGACGTACAATGTACCC; SEQ. ID NO. 11: AACTACATGGTATGTGGTGAACTAAACCATTCTTGTCTCGCATTTTTCTCTTTTATAT TAT-TTGACGTACAATGTACCC; SEQ. ID NO. 12: AACTACATGGTATGTGGTGAACTCACGCGCATAACCCTTTTTTCACCTGCCCTTTTAA CTAATGACGTACAATGTACCC; SEQ. ID NO. 13: AACTACATGGTATGTGGTGAACTGCCATAAGATGACGACATTCATCACCAAACCAA CCTCAGCGACGTACAATGTACCC; or SEQ. ID NO. 14: AACTACATGGTATGTGGTGAACTGCCGGGTGATTGAAAAGCAGATTACCGATCATCC AATAAAGACGTACAATGTACCC.

2. The aptamer of claim 1, wherein the aptamer is linked to a surface.

3. The aptamer of claim 1, wherein the aptamer is linked to an antisense strand that is complimentary to at least a portion of the aptamer.

4. An aptamer with high affinity to LDL particles and high selectivity for LDL particles over HDL particles, wherein the aptamer includes a sequence selected from one of: SEQ. ID NO. 10: AACTACATGGTATGTGGTGAACTAACCTTAATTTACCCTTGTTTTATCATTTCCATCA TAGCTGACGTACAATGTACCC; SEQ. ID NO. 11: AACTACATGGTATGTGGTGAACTAAACCATTCTTGTCTCGCATTTTTCTCTTTTATAT TAT-TTGACGTACAATGTACCC; SEQ. ID NO. 12: AACTACATGGTATGTGGTGAACTCACGCGCATAACCCTTTTTTCACCTGCCCTTTTAA CTAATGACGTACAATGTACCC; SEQ. ID NO. 13: AACTACATGGTATGTGGTGAACTGCCATAAGATGACGACATTCATCACCAAACCAA CCTCAGCGACGTACAATGTACCC; or SEQ. ID NO. 14: AACTACATGGTATGTGGTGAACTGCCGGGTGATTGAAAAGCAGATTACCGATCATCC AATAAAGACGTACAATGTACCC.

5. The aptamer of claim 4, wherein the aptamer is linked to a surface.

6. The aptamer of claim 4, wherein the aptamer is linked to an antisense strand that is complimentary to at least a portion of the aptamer.

* * * * *

SEQUENCE LISTING

```
<160> NUMBER OF SEQ ID NOS: 14

<210> SEQ ID NO 1
<211> LENGTH: 40
<212> TYPE: DNA
<213> ORGANISM: Artificial Sequence
<220> FEATURE:
<223> OTHER INFORMATION: Aptamer to LDL

<400> SEQUENCE: 1
acctcgattt tatattattt cgcttaccaa caactgcaga                          40

<210> SEQ ID NO 2
<211> LENGTH: 40
<212> TYPE: DNA
<213> ORGANISM: Artificial Sequence
<220> FEATURE:
<223> OTHER INFORMATION: Aptamer to LDL

<400> SEQUENCE: 2
gtcagcttct tctatataat tcaccttgcc tctcgttcct                          40
```

```
<210> SEQ ID NO 3
<211> LENGTH: 40
<212> TYPE: DNA
<213> ORGANISM: Artificial Sequence
<220> FEATURE:
<223> OTHER INFORMATION: Aptamer to LDL

<400> SEQUENCE: 3
aaccttaatt tacccttgtt ttatcatttc catcatagct                    40

<210> SEQ ID NO 4
<211> LENGTH: 40
<212> TYPE: DNA
<213> ORGANISM: Artificial Sequence
<220> FEATURE:
<223> OTHER INFORMATION: Aptamer to LDL

<400> SEQUENCE: 4
aaaccattct tgtctcgcat ttttctcttt tatattattt                    40

<210> SEQ ID NO 5
<211> LENGTH: 40
<212> TYPE: DNA
<213> ORGANISM: Artificial Sequence
<220> FEATURE:
<223> OTHER INFORMATION: Aptamer to LDL

<400> SEQUENCE: 5
cacgcgcata acccttttt cacctgccct tttaactaat                     40

<210> SEQ ID NO 6
<211> LENGTH: 40
<212> TYPE: DNA
<213> ORGANISM: Artificial Sequence
<220> FEATURE:
<223> OTHER INFORMATION: Aptamer to LDL

<400> SEQUENCE: 6
gccataagat gacgacattc atcaccaaac caacctcagc                    40

<210> SEQ ID NO 7
<211> LENGTH: 40
<212> TYPE: DNA
<213> ORGANISM: Artificial Sequence
<220> FEATURE:
<223> OTHER INFORMATION: Aptamer to LDL

<400> SEQUENCE: 7
gccgggtgat tgaaaagcag attaccgatc atccaataaa                    40

<210> SEQ ID NO 8
<211> LENGTH: 79
<212> TYPE: DNA
<213> ORGANISM: Artificial Sequence
<220> FEATURE:
<223> OTHER INFORMATION: Aptamer to LDL

<400> SEQUENCE: 8
aactacatgg tatgtggtga actacctcga ttttatatta tttcgcttac caacaactgc    60
agagacgtac aatgtaccc                                               79

<210> SEQ ID NO 9
<211> LENGTH: 79
<212> TYPE: DNA
<213> ORGANISM: Artificial Sequence
```

<220> FEATURE:
<223> OTHER INFORMATION: Aptamer to LDL

<400> SEQUENCE: 9
aactacatgg tatgtggtga actgtcagct tcttctatat aattcacctt gcctctcgtt    60
cctgacgtac aatgtaccc                                                 79

<210> SEQ ID NO 10
<211> LENGTH: 79
<212> TYPE: DNA
<213> ORGANISM: Artificial Sequence
<220> FEATURE:
<223> OTHER INFORMATION: Aptamer to LDL

<400> SEQUENCE: 10
aactacatgg tatgtggtga actaacctta atttaccctt gttttatcat ttccatcata    60
gctgacgtac aatgtaccc                                                 79

<210> SEQ ID NO 11
<211> LENGTH: 79
<212> TYPE: DNA
<213> ORGANISM: Artificial Sequence
<220> FEATURE:
<223> OTHER INFORMATION: Aptamer to LDL

<400> SEQUENCE: 11
aactacatgg tatgtggtga actaaaccat tcttgtctcg cattttctc ttttatatta     60 tttgacgtac aatgtaccc                                                 79

<210> SEQ ID NO 12
<211> LENGTH: 79
<212> TYPE: DNA
<213> ORGANISM: Artificial Sequence
<220> FEATURE:
<223> OTHER INFORMATION: Aptamer to LDL

<400> SEQUENCE: 12
aactacatgg tatgtggtga actcacgcgc ataacccttt tttcacctgc cctttaact     60 aatgacgtac aatgtaccc                                                 79

<210> SEQ ID NO 13
<211> LENGTH: 79
<212> TYPE: DNA
<213> ORGANISM: Artificial Sequence
<220> FEATURE:
<223> OTHER INFORMATION: Aptamer to LDL

<400> SEQUENCE: 13
aactacatgg tatgtggtga actgccataa gatgacgaca ttcatcacca aaccaacctc    60
agcgacgtac aatgtaccc                                                 79

<210> SEQ ID NO 14
<211> LENGTH: 79
<212> TYPE: DNA
<213> ORGANISM: Artificial Sequence
<220> FEATURE:
<223> OTHER INFORMATION: Aptamer to LDL

<400> SEQUENCE: 14
aactacatgg tatgtggtga actgccgggt gattgaaaag cagattaccg atcatccaat    60
aaagacgtac aatgtaccc                                                 79